(12) United States Patent
Hotto et al.

(10) Patent No.: US 8,652,029 B2
(45) Date of Patent: Feb. 18, 2014

(54) INTELLIGENT ENDOSCOPE SYSTEMS AND METHODS

(71) Applicants: Robert Hotto, Carlsbad, CA (US); Nelson Powell, Atherton, CA (US)

(72) Inventors: Robert Hotto, Carlsbad, CA (US); Nelson Powell, Atherton, CA (US)

(*) Notice: Subject to any disclaimer, the term of this patent is extended or adjusted under 35 U.S.C. 154(b) by 0 days.

(21) Appl. No.: 13/911,400

(22) Filed: Jun. 6, 2013

(65) Prior Publication Data

US 2013/0289348 A1    Oct. 31, 2013

Related U.S. Application Data

(63) Continuation of application No. 12/794,577, filed on Jun. 4, 2010, now abandoned.

(51) Int. Cl.
*A61B 1/00* (2006.01)
*A61B 1/04* (2006.01)

(52) U.S. Cl.
USPC .......................................................... 600/121

(58) Field of Classification Search
USPC ................. 600/121, 123, 140, 153, 169, 117
See application file for complete search history.

(56) References Cited

U.S. PATENT DOCUMENTS

| | | | |
|---|---|---|---|
| 5,779,625 A * | 7/1998 | Suzuki et al. | 600/121 |
| 2009/0044799 A1 * | 2/2009 | Qiu | 128/200.26 |
| 2009/0143651 A1 * | 6/2009 | Kallback et al. | 600/301 |
| 2010/0185055 A1 * | 7/2010 | Robertson et al. | 600/117 |

* cited by examiner

*Primary Examiner* — Philip R Smith
(74) *Attorney, Agent, or Firm* — Denko Coburn Lauff LLP

(57) ABSTRACT

Endoscope sheaths and associated endoscopy data collection and analysis systems and methods are described. In one implementation an endoscope sheath include a body and one or more sensors disposed in the body. The sheath may further include a leak detection apparatus configured to detect leaks in the sheath body. In addition, the sheath may include actuator apparatus, such as a balloon catheter or other surgical instrument. Data from the endoscope and endoscope sheath may be collected, fused and displayed for use in medical procedures and/or analysis.

6 Claims, 28 Drawing Sheets

Example Sensor Enhanced Endoscopy System

*One Embodiment of a Position Sensing Detector*

*Example Sensor Enhanced Endoscopy System*

*Exemplary Embodiment with Position Location Element (Magnet, Coil, Hall Effect Sensor, etc.)*

*Exemplary Endoscope with Dimensional
Ultrasonic Measurement Element*

Cross-Sectional Image

Sensory Data Matched to Image

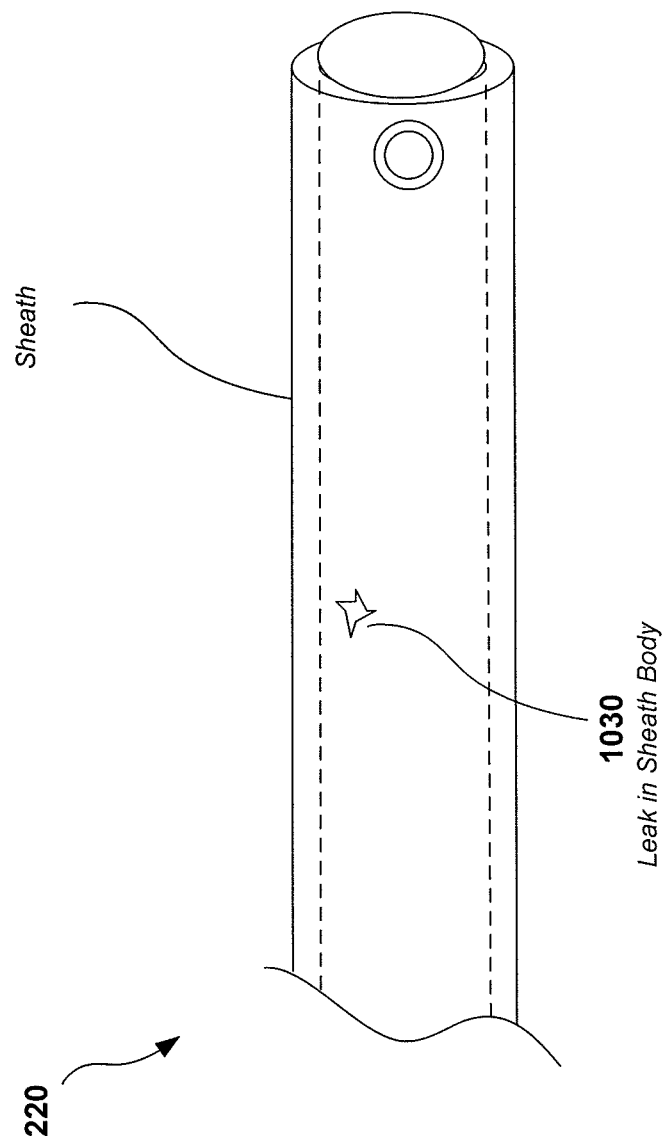

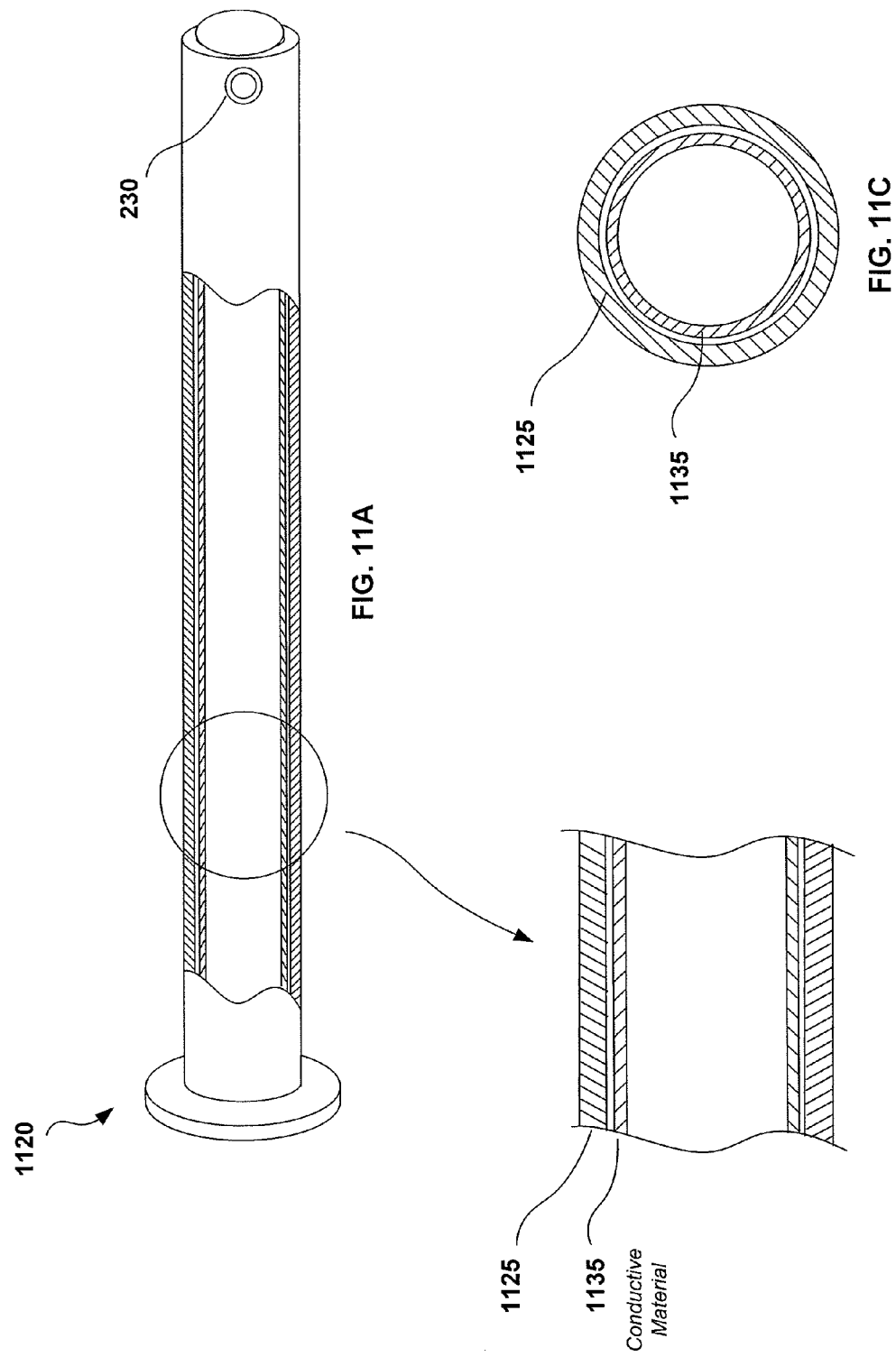

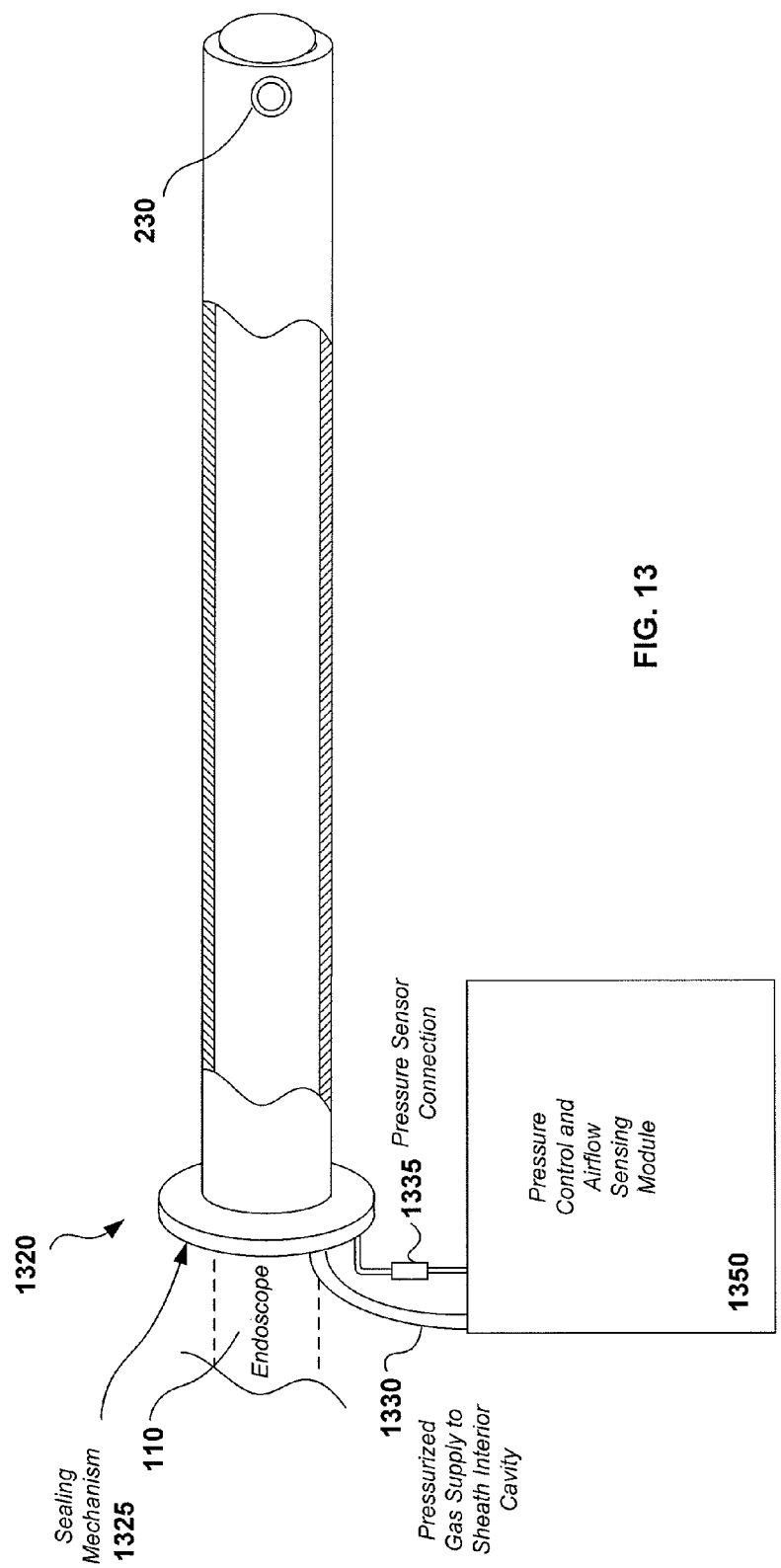

Balloon Retracted

Balloon Deployed

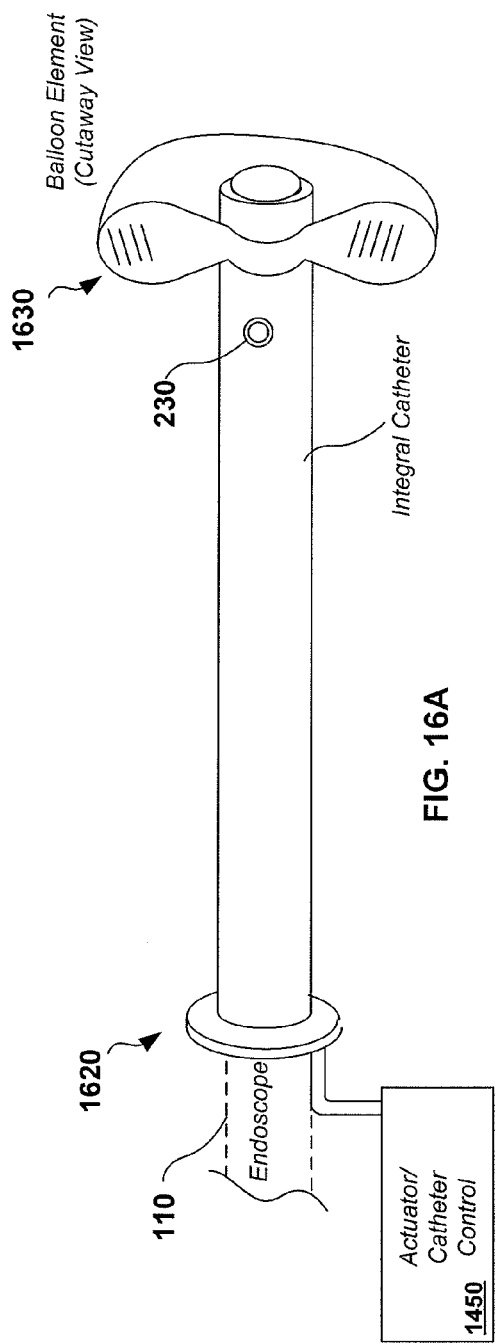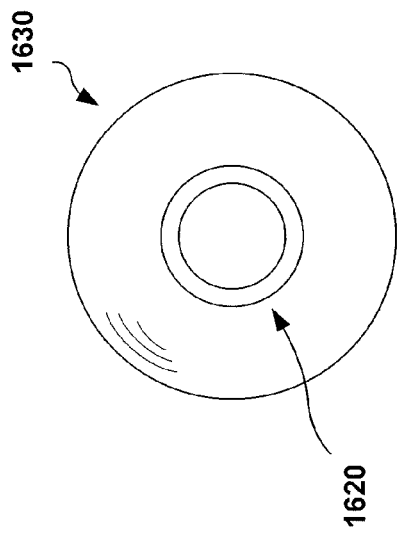
FIG. 16A
FIG. 16B

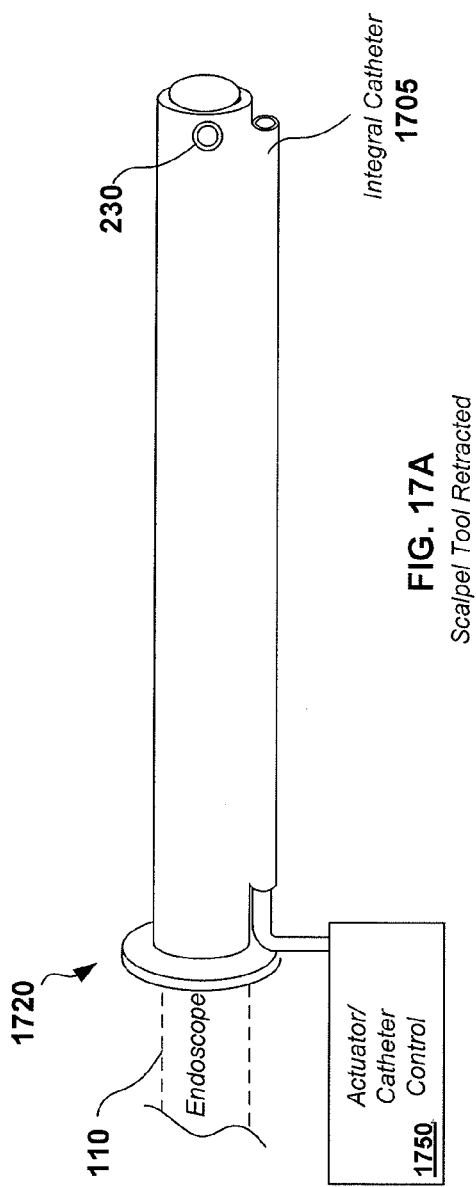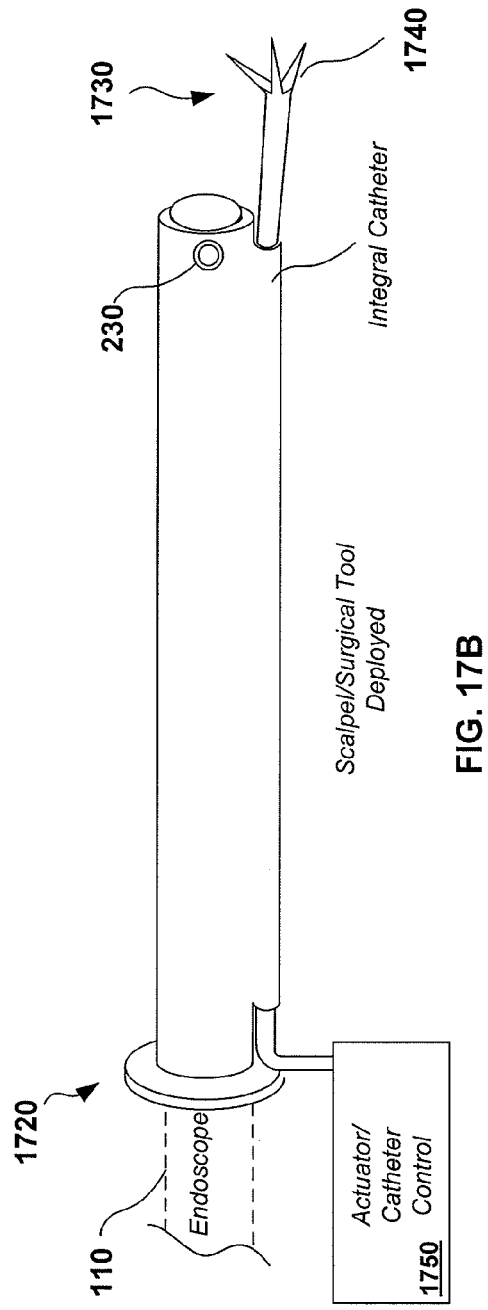

INTELLIGENT ENDOSCOPE SYSTEMS AND METHODS

FIELD OF THE INVENTION

The present invention relates generally to endoscopy and endoscope sheaths. More particularly but not exclusively, the invention relates to endoscopy sheath apparatus and methods aided by sensors such as pressure, temperature, position detection sensors, leak detection sensors, acoustic sensors and/or other types of sensors, as well as actuators such as balloon actuators, catheters and/or surgical instrument actuators.

BACKGROUND

Endoscopy has been used for a variety of diagnostic and surgical procedures in the medical field, as well as other non-medical fields, for many years. In a typical medical endoscopy procedure, an endoscope, which commonly includes a body having flexible and/or rigid structural elements along with an imaging element such as a camera and/or lens assembly and lighting, is inserted into a body orifice such as the nose, throat, or rectum and is then positioned to view conditions inside the body. Some endoscopes are configured in an ingestible pill form (denoted herein as "pill-type" endoscopes to distinguish them from traditional endoscopes) that is swallowed and travels through the body while collecting diagnostic information.

In order to prevent introduction of germs or other foreign matter into the body, endoscopes are frequently reprocessed using sterilization equipment, disinfected in a germicidal solution or enclosed by a sheath, which is typically made of a pliable material which conforms to the shape of the endoscope body and isolates any contamination from the endoscope. Currently used endoscope sheaths are costly, one time use disposable components that primarily act as passive covers for the endoscope, without providing any additional diagnostic functionality. Moreover, in many cases, endoscope sheaths may act to limit or inhibit endoscope functionality by imposing a barrier between the endoscope and the patient's body part being examined. For example, components incorporated into the endoscope, such as imaging elements, may have reduced optical performance due to the sheath and condensation that may occur between the sheath and the endoscope lens. Sensor integral to the endoscope may also be rendered non-functional when covered by the sheath.

Problems with endoscope and sheath sterilization have received attention from organizations such as the FDA and CDC, which have promulgated publications including "Guidance for Manufacturers Seeking Marketing Clearance of Ear, Nose and Throat Endoscope Sheaths Used as Protective Barriers," at //www.fda.gov/MedicalDevices/DeviceRegulationandGuidance/GuidanceDocuments/ucm073746.htm, "FDA and CDC PUBLIC HEALTH ADVISORY, Infections from Endoscopes Inadequately Reprocessed by an Automated Endoscope Reprocessing System," at http://www.olympusamerica.com/msg_section/files/FDAadvisory.pdf, "FDA Public Health Notification: Updated Information on Customer Ultrasonics, Inc., Endoscope Washer/Disinfectant." at http://www.fda.gov/MedicalDevices/Safety/AlertsandNotices/PublicHealthNotifications/UCM062075. Concerns have led to investigations of the value of sheaths as barrier functions for endoscopy, see, e.g., EVALUATION OF PROTOCOLS FOR TESTING ENDOSCOPE SHEATHS AS VIRAL BARRIERS, Baker, et al., FDA Science Forum, 1997, which is incorporated by reference herein.

While sheaths have been used for some time in endoscopy, they have not been used to provide other sensory inputs or actuator functions to improve diagnosis and treatment. Accordingly, there is a need in the art for improved endoscope sheaths, as well as associated medical diagnostic, analytic and treatment techniques.

SUMMARY

The present invention is directed generally towards endoscope sheaths and endoscopy systems and methods.

In one aspect, the present invention relates to an endoscope sheath comprising a body and one or more sensor elements. The sheath may include a leak detection apparatus and/or an integral actuator apparatus.

In another aspect, the present invention relates to an endoscope sheath, comprising a body including an exterior surface, an interior surface and a cavity bounded by the interior surface, the cavity disposed for receiving an endoscope and one or more sensors disposed in the body.

In another aspect, the present invention relates to an endoscope sheath, comprising a body including an exterior surface, an interior surface and a cavity bounded by the interior surface, the cavity disposed for receiving an endoscope and a leak detection apparatus configured to detect a leak in the body.

In another aspect, the present invention relates to an endoscope sheath, comprising a body including an exterior surface, an interior surface and a cavity bounded by the interior surface, the cavity disposed for receiving an endoscope; and an actuator apparatus disposed in the sheath body.

In another aspect, the present invention relates to a system for performing endoscopy, comprising an endoscopy sheath, said endoscope sheath including one or more sensors and an endoscopy analysis module, said analysis module including: a processor, a memory coupled to the processor and an input module coupled to the processor, wherein the processor is configured to: receive data from the one or more sensors, receive data from an endoscope coupled to the analysis module, fuse the data from the one or more sensors and the data from an endoscope and stored the fused data in the memory.

In another aspect, the present invention is related to a machine readable medium containing instructions for execution by a computer to receive data from one or more sensors disposed on an endoscope sheath, receive data from an endoscope, fuse the data from the one or more sensors and the data from an endoscope and stored the fused data in a memory.

In another aspect, the present invention is related to a method of performing an endoscopy procedure, comprising generating sensor data from a body cavity of a patient, wherein the sensor data is provided from one or more sensors disposed on an endoscope sheath positioned on an endoscope and providing the sensor data to a endoscopy analysis module.

Additional aspects of the present invention are described below in conjunction with the appended drawings.

BRIEF DESCRIPTION OF THE DRAWINGS

For a better understanding of the nature and objects of various embodiments of the invention, reference should be made to the following detailed description taken in conjunction with the accompanying drawings, wherein:

FIG. 10 illustrates an example of a leak in a smart sheath;

FIGS. 11A-11C illustrate details of an embodiment of a smart sheath including a leak detection apparatus;

FIG. 13 illustrates details of embodiments of pneumatic leak detection details;

FIGS. 16A and 16B illustrate details of an embodiment of an endoscope sheath with integral actuator apparatus;

FIGS. 17A and 17B illustrate details of an embodiment of an endoscope sheath with integral actuator apparatus.

DETAILED DESCRIPTION OF EMBODIMENTS

The present invention is directed generally towards endoscope sheaths and endoscopy systems and methods.

In one aspect, the present invention relates to an endoscope sheath comprising a body and one or more sensor elements. The sheath may include a leak detection apparatus and/or an integral actuator apparatus. In another aspect, the present invention relates to an endoscope sheath, comprising a body including an exterior surface, an interior surface and a cavity bounded by the interior surface, the cavity disposed for receiving an endoscope and one or more sensors disposed in the body. In another aspect, the present invention relates to an endoscope sheath, comprising a body including an exterior surface, an interior surface and a cavity bounded by the interior surface, the cavity disposed for receiving an endoscope and a leak detection apparatus configured to detect a leak in the body.

In another aspect, the present invention relates to an endoscope sheath, comprising a body including an exterior surface, an interior surface and a cavity bounded by the interior surface, the cavity disposed for receiving an endoscope; and an actuator apparatus disposed in the sheath body. In another aspect, the present invention relates to a system for performing endoscopy, comprising an endoscopy sheath, said endoscope sheath including one or more sensors and an endoscopy analysis module, said analysis module including: a processor, a memory coupled to the processor and an input module coupled to the processor, wherein the processor is configured to: receive data from the one or more sensors, receive data from an endoscope coupled to the analysis module, fuse the data from the one or more sensors and the data from an endoscope and stored the fused data in the memory.

In another aspect, the present invention is related to a machine readable medium containing instructions for execution by a computer to receive data from one or more sensors disposed on an endoscope sheath, receive data from an endoscope, fuse the data from the one or more sensors and the data from an endoscope and stored the fused data in a memory. In another aspect, the present invention is related to a method of performing an endoscopy procedure, comprising generating sensor data from a body cavity of a patient, wherein the sensor data is provided from one or more sensors disposed on an endoscope sheath positioned on an endoscope and providing the sensor data to a endoscopy analysis module. Additional aspects are described below in conjunction with the appended drawings.

Various embodiments of the present invention may be implemented using techniques for detection and monitoring of fluid flow and/or pressure. Various aspects of implementations of such detection and monitoring are described in U.S. Pat. Nos. 6,408,682, 6,412,334, 7,353,692 and 5,008,616. The content of each of these patents is incorporated by reference herein in its entirety.

Figure 1:
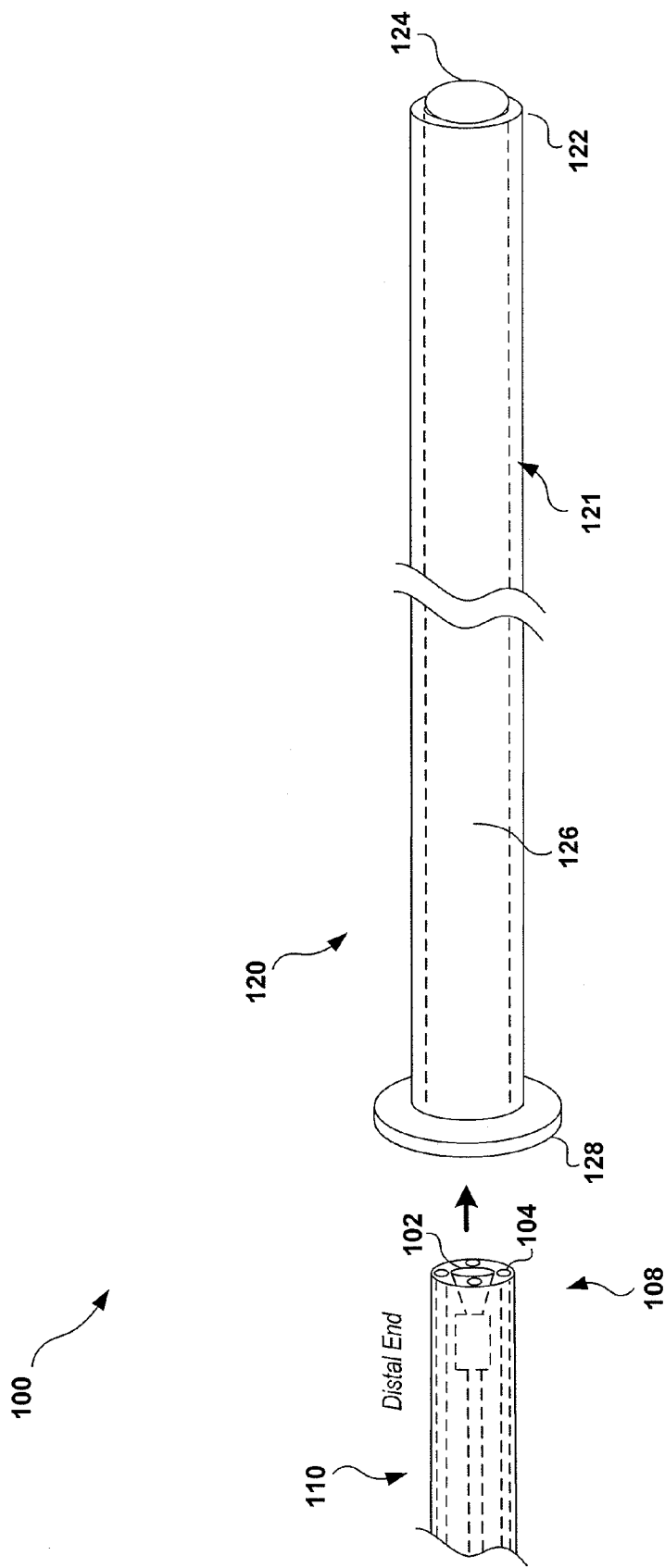
FIG. 1 illustrates an example endoscope and associated endoscope sheath.

Endoscopy has been used in a variety of medical diagnostic and treatment applications to view details inside the body of a patient, as well as for various other non-medical application. FIG. 1 illustrates a simplified view of a typical prior art endoscopy system 100 that includes an endoscope 110 and an endoscope sheath 120. Typical endoscopes, such as endoscope 110, include a body having flexible and/or rigid mechanical structures for allowing the device to be inserted in an opening in the patient's body, such as the nose, mouth, rectum or an incision in the body, and then manipulated once inside the body to view various internal features. A typical endoscope also includes a handle and other mechanical and electrical components (not shown), coupled at the proximal end (not shown) of the instrument to facilitate insertion of the endoscope into the body and visualization of the area being diagnosed or treated.

The endoscope's visualization function may be facilitated by an imaging element 102, such as a lens or camera element, positioned in the distal end 108 of the endoscope, which may be accompanied by a light emitting element 104, such as a light source, LED, optical fiber, and the like, to illuminate the area of interest.

In addition, endoscopy system 100 may include an endoscope sheath 120. Endoscope sheath 120 is provided to facilitate prevention of contamination to a patient and/or endoscope, such as by cross-infection through exchange of biological material between patients, as well as to maintain endoscope sterilization by providing a physical barrier between the endoscope 110 and the patient's body. A typical endoscope sheath is configured similar to a balloon or condom, including a body 121, typically comprising a thin, pliable material having an outer surface exposed to the patient's body and tissues, and an inner surface exposed to the endoscope. Endoscope sheath 120 is configured with a hollow inner cavity or lumen 126 to facilitate receipt of the endoscope when inserted into the sheath, a proximal end 128 configured to be positioned outside the patient's body during an endoscopic procedure, a distal end 122 configured to be positioned adjacent to the corresponding distal end of the endoscope 110, and an optical port 124, configured to provide transparency and/or filtering to the imaging element 102 and/or light emitting element 104 when the endoscope 110 is inserted into the sheath 120. Endoscope sheaths are typically more costly to use than germicidal solutions and are a disposable item, for one time use, with little to no functionality beyond isolating the exterior of the endoscope from direct contact with the patient.

Figure 2A:
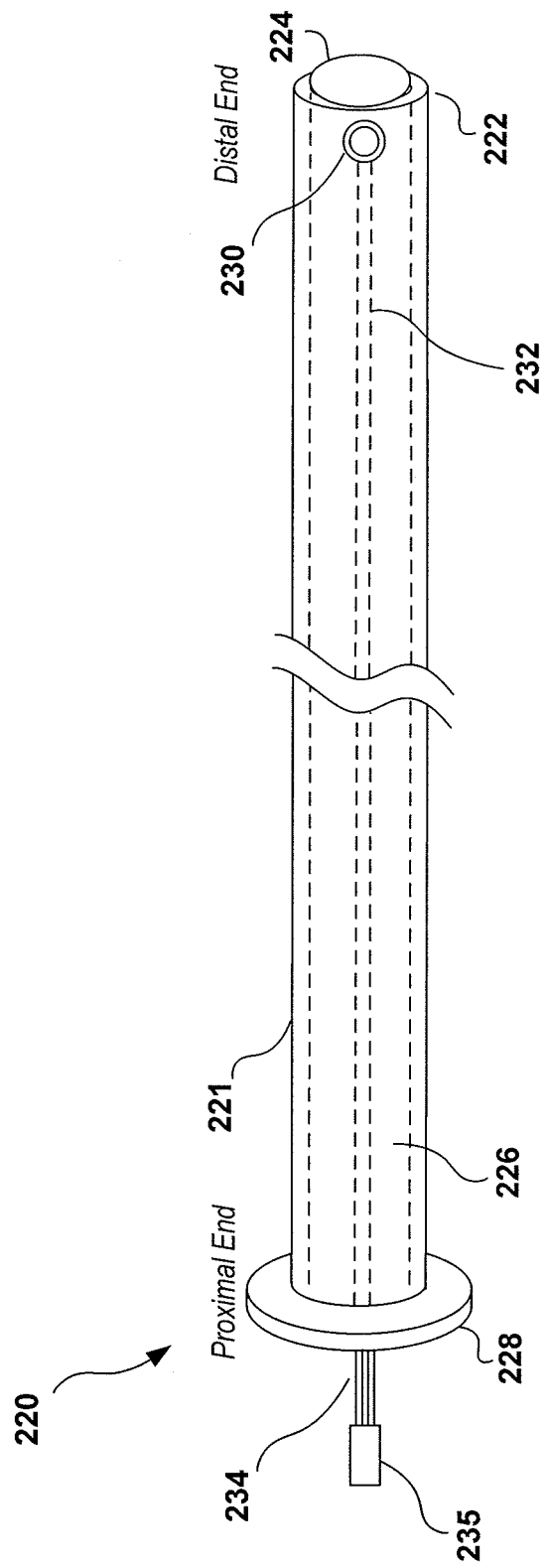
FIG. 2A illustrates one embodiment of an endoscope sheath including an integrated sensor element in accordance with aspects of the present invention.

Attention is now directed to FIG. 2A, which illustrates one embodiment of an endoscope sheath 220 in accordance with aspects of the present invention. As shown in FIG. 2A, an endoscope sheath may include a body similar to that shown in FIG. 1, as well as one or more sensor elements 230, as well as other elements (not shown in FIG. 2A), disposed in the sheath body to facilitate sensing of desired parameters or physical conditions of interest during an endoscopy procedure. The sheath body will generally include an exterior surface and interior surface, with the body typically formed to match and cover the associated endoscope in substantially its entirety. However, in some embodiments, the sheath body may be made so as to cover only part of the endoscope. In some implementations, the sheath may be made so as to have openings at both ends, and may also include sealing mechanisms at one or both ends of the sheath body to seal the part of the endoscope that is enclosed. Other body shapes may be used in some embodiments, with the body shape configured to accommodate one or more sensor elements such as are further described below.

In some implementations, the sheath body may comprise a flexible or semi-flexible material. Body materials may comprise latex, nitrile, plastics, polymers, rubber materials or other materials known or developed for use in medical applications. Likewise, for other endoscopy applications, materials may be plastics, rubbers, polymers or other materials suitable for such applications, such as materials for corrosive environments, contaminated environments, toxic environments, and the like. In some embodiments, the sheath body may comprise a rigid or substantially rigid material rather than a flexible material.

Sensor elements disposed in the sheath body may be configured so as to provide sensing contact with a space exterior to the sheath, such as an airway between the sheath and a patient's throat or other body orifice, a blood vessel in a vascular implementations, or other body orifices such as those in the digestive system or excretory system. In some implementations, sensors may be disposed in the body so as to be in contact with a space interior to the sheath, such as a space between the interior surface of the sheath and an inserted endoscope. Sensors may be disposed in the body by attachment to the body on the interior or exterior, such as by use of adhesives or other attachment materials, by molding or forming into the body, or by other attachment or forming methods known or developed in the art.

Physical conditions of interest may include pressure, temperature, flow rate (based on, for example, flow of a gas such as air through an airway or fluid, such as blood, through a flow channel such as an artery or vein), pH, cross-sectional distance measurements (such as measurement of cross-sectional areas of a gas or liquid flow channel, such as the nasal passages or throat), acoustic information (audible sounds or other acoustic information), blood pressure, pulse, and the like.

In an exemplary embodiment, sensor element 230 comprises a pressure sensor, configured to measure pressure at or near a location being imaged by the endoscope. Pressure sensor 230 may also include one or more additional sensor elements. For example, in one embodiment, sensor element 230 comprises a pressure sensor and temperature sensor, such as a MEMS based circuit like the SCP1000 device manufactured by VTI Technologies, which is configured to measure both pressure and temperature at or near the location being imaged. Other similar or equivalent devices known or developed in the art may also be used in various implementations.

Research and analysis by the inventors of the technology disclosed herein in the area of airway physiology and airflow characteristics has shown a relationship between pressure values and airflow restrictions in breathing channels, such as through airways like the nose, palate, and rear portion of the mouth and throat. These may be associated with conditions such as airway restriction and sleep apnea, or other breathing issues. While a conventional endoscope may provide some visualization of an airway restriction, additional information of value may be added by acquiring pressure data, acoustic data, body conditions such as blood pressure, pulse, temperature and/or other sensor data simultaneously with visual information such as images or video provided by the endoscope. In particular, it may be advantageous to obtain this additional sensory information and map or fuse it to the associated imaging data obtained by the endoscope camera to provide an image or display of the combined data and image or images in two or three dimensions.

In addition to pressure and/or temperature data, other data and information, such as the physical condition parameters described above or others, may be used in some embodiments to provide additional diagnostic and/or treatment information. For example, the sensor may include an acoustic sensing element such as a microphone or other acoustic sensing element to detect audible, sub-audible or ultrasonic sounds. The sensor may include a pH sensor, such as, for example, a pH sensor based on the National Semiconductor LMC6001 and shown in the associated datasheet. Various other sensor elements as are known or developed in the art may also be used in various embodiments.

Further, in addition to configurations of single sensors disposed in a sheath body, two or three dimensional arrays of sensors may be desirable to generate sensory profiles over a surface, area or volume of the patients body. For example, by using multiple pressure sensors configured such as shown in the array configurations of FIG. 3A, 3B, 3C, or in other two dimensional or three dimensional configurations, flow rates and profiles may be determined over those areas, surfaces or volumes. This enables a user such as a medical doctor to relate visual information to sensory data from the body region being diagnosed. In some embodiments, images, pressure data, temperature data, acoustic data, and/or other data such as airflow rates, pH, and/or other diagnostic parameters, may be determined at a particular position within the body cavity being imaged and may then be mapped or fused together to provide more comprehensive data and information for display and/or analysis. In addition, information regarding airway dimensional parameters as cross-sectional dimensions, area and/or volume may also be obtained through measurement sensing elements so at to add dimensional data to the diagnostic data. Dimensional measurements may be obtained by incorporating one or more ultrasonic, optical, mechanical and/or other measuring elements in the endoscope sheath, along with the other sensory elements described above.

In some implementations, actuator apparatus may also be added to a sheath. These may be inflatable actuator mechanisms such as balloon catheters, or may be other actuator mechanisms such as scalpels, abrasion instruments, ultrasonic or acoustic elements, thermal (i.e., heating or cooling elements), ablation instruments, stent placement instruments, or other actuator apparatus known or developed in the art. In some cases, multiple actuator elements, such as a balloon catheter, surgical cutting tool such as a scalpel, or placement tool, such as a shunt placement tool, may be incorporated as actuator apparatus in the sheath. For example, in a vascular application, a sheath may include a first actuator apparatus for deploying a balloon catheter and a second actuator apparatus for placing a stent, basket or other embedded device.

Returning to FIG. 2A, As further shown, sheath 220 may include a channel 232 for positioning sensor signal or data transmission apparatus, such as signal wires, optical fibers or other means of transmitting sensor signals and/or data. Channel 232 may also facilitate power transmission to the sensor 230 from the endoscope 110 or a connector coupled to the endoscope 110 or a battery or external source, such as a power supply, battery, and the like. Sheath 220 may include an optical port 224, which may be configured as a clear port for providing viewing from an imaging element of the endoscope, or may be a lens or other optical apparatus for providing or enhancing imaging.

In addition, in some embodiments, sensor 230 may be configured to operate via wireless transmission mechanisms, such as through radio frequency (RF) signals, acoustic signaling, or other non-wired signaling techniques, and the sensor may be battery powered or provided with power via wiring in the sheath. Likewise, while sensor 230 may be powered by wires or batteries positioned in cavity 226 and/or channel 232, sensor 230 may also be powered by scavenged power, such as may be provided through RF, acoustic, optical or other scavenged power mechanisms.

Sensor 230 will typically provide sensed signals and/or data via digital or analog signaling mechanisms such as those known or developed in the art. For example, in one embodiment, sensor 230 is configured to provide digital data through a serial connection, such as an SPI serial interface comprising conductors/wires 234, that can accommodate reading of one or more sensors through an electrical bus connector provided at the proximal end of sheath 220 to be coupled to the endoscope 110 and/or external electronic devices, such as a signal recorder, display device, or other medical diagnostic instrument or data recorder. Sensor 230 may also provide one or more analog signals via wires 234 (or via other mechanisms, such as wireless transmission) to be processed and/or displayed by external electronic diagnostic or storage devices. Alternately, signaling may be done via nonelectrical connections 234, such as via optical fibers. As noted previously, connections 234 may be disposed in channel 232 to facilitate smooth insertion of sheath 220 in an endoscope.

It is noted that, while shown on the outer surface of sheath 220 near the distal end, sensor element 230 need not be positioned only at this location, but may alternately be positioned at any of various positions around the circumference or longitudinal axis of sheath 220, as illustrated in FIG. 3. For example, in some embodiments sensor element 230 may be positioned near the distal end of sheath 220 on the side (as shown in FIG. 2A), while in other embodiments the sensor element may be positioned midway along the sheath (not shown in FIG. 2A), at the distal end adjacent to element 224 (not shown in FIG. 2A), or at other positions on or in sheath 220. In some embodiments, sensor element 230 may be positioned on the end of the sheath 220, adjacent to or within an optical port 224. In some cases, sensor element 230 may be placed on or within an actuator mechanism included in the sheath.

Sheath 220 may include one or more graduations disposed on or within the sheath body to facilitate position determination of the sheath during a procedure. For example, the sheath may include graduations on the service to identify the position of the sheath during a procedure via ultrasonic, electromagnetic, optic, or other measurement and positioning mechanisms. These may be painted or impregnated on or within the sheath body using materials that may be imaged by x-rays, catscans, MRIs or other imaging technologies.

Figure 2C:
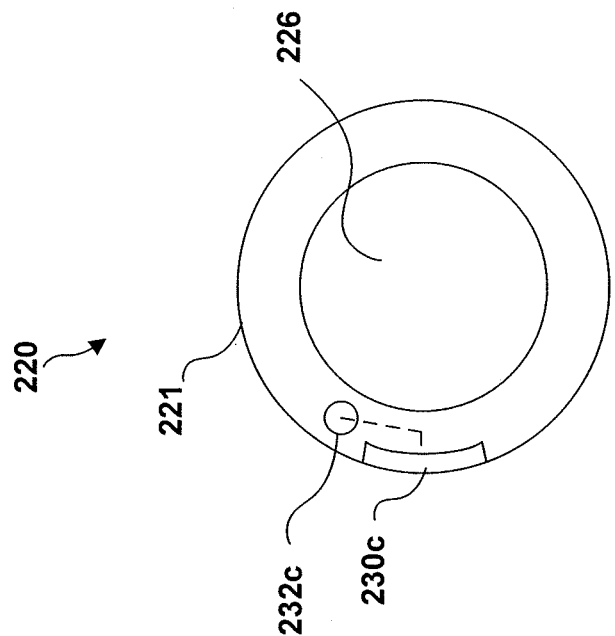
FIG. 2C illustrates another embodiment of a cross-section of an endoscope sheath as shown in FIG. 2A, in accordance with aspects of the present invention.

Sheath 220 may include one or more connectors 235 at or near the proximal end 228 to facilitate connection of the sensor elements to the endoscope handle, other endoscope electronics, processing components, or external devices (not shown). Connector 235 may comprise a single connector or a plurality of connectors with separate connections for signal, power or other inputs or outputs. For example, FIG. 2D illustrates one embodiment wherein one or more connectors 235 comprise a power connector 235a configured to couple to a power supply or power device such as battery 260. Alternately, the battery 260 may be mounted on or integral with the sheath 220. For example, the battery may be incorporated into a recess in the sheath or may be integrally formed in the sheath for disposal after use. Other techniques known in the art for scavenging power, such as via chemical reactions within the body, photovoltaic power, and the like may also be used.

One or more additional signal connectors 235b are also provided to couple to one or more signal and/or data connections. It is further noted that signal connectors 235, 235a and/or 235b may be configured to connect to additional connectors (such as an endoscope connectors) within the sheath 220 and/or externally from sheath 220 and may be incorporated into the sheath 220. Likewise, battery 260 (or other power supply devices) may be incorporated into the endoscope or sheath 220 or may be external to the endoscope and/or sheath 220.

Figure 2B:
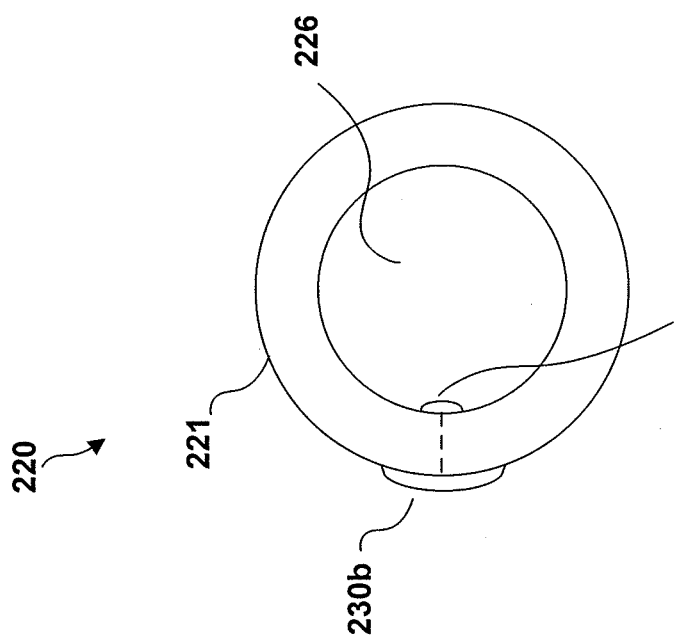
FIG. 2B illustrates one embodiment of a cross-section of an endoscope sheath as shown in FIG. 2A, in accordance with aspects of the present invention.
Figure 2D:
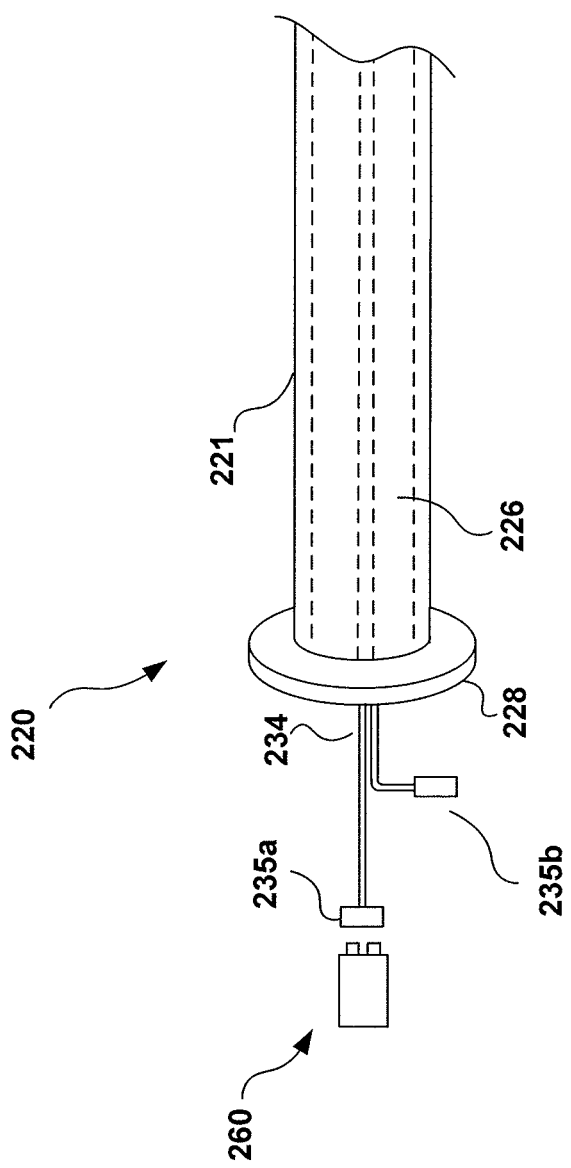
FIG. 2D illustrates one embodiment of a connector configuration for an endoscope sheath, in accordance with aspects of the present invention.
Figure 2E:
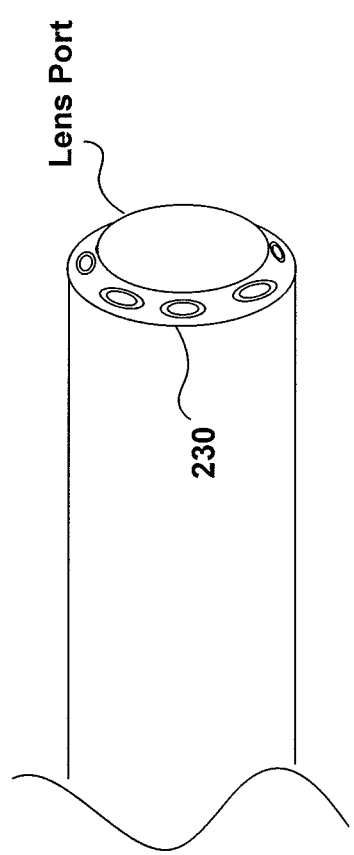
FIG. 2E illustrates one embodiment of a sensor element for an endoscope, in accordance with aspects of the present invention.

Attention is now directed to FIG. 2B which illustrates one embodiment of a cross section of a sheath 220. In this embodiment, the sensor element 230b is positioned on the external surface 221 of the sheath 220. Signal wires or other transmission mechanisms, such as thin film conductive wires or other signaling mechanisms (if used), are then routed through the wall of the sheath to channel 232b, which may be positioned on the interior cavity 226 of the sheath, in proximity to the endoscope 110 when mounted in the sheath. Alternately, the sensor element may be positioned all or partially within the sheath body, and the signaling wires may be routed internal to or within the sheath body.

FIG. 2C illustrates an alternate embodiment of a cross section of a sheath 220, which shows sensor element 230c positioned inside of, or recessed in a slot or other depression in the outer surface 221 of the sheath, or glued or affixed to the surface. Sensor 230c may, for example, be molded into sheath 220, or inserted into a recess in the outer surface 221 of the sheath. Wiring to the sensor, if used, may also be routed internal to the sheath, through a channel 232c formed or molded in the sheath. It is further noted that combinations of elements as shown in FIG. 2B and FIG. 2C may also be used in various embodiments, and in some embodiments wherein wireless sensor information is transmitted, channel 232 may be omitted.

Figure 3A:
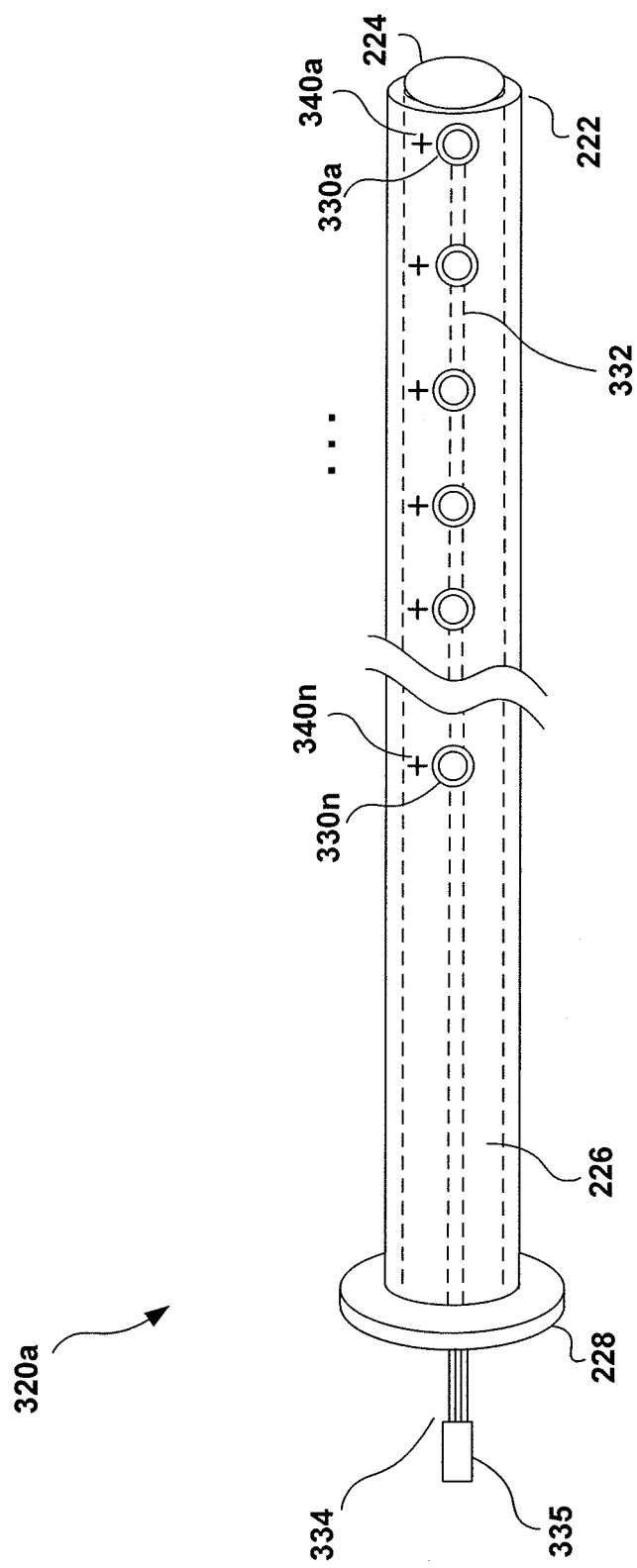
FIGS. 3A-3C illustrate various embodiments of an endoscope sheath including a plurality of sensor elements, in accordance with aspects of the present invention.

Attention is now directed to FIG. 3A which illustrates another embodiment of the present invention, wherein a plurality of sensors are provided on or within an endoscope sheath 320. As shown in FIG. 3A, sensor elements 330a through 330n, where n is 2 or more, may be positioned on or within sheath 320 to provide additional sensor data or signals. Sensors 330a through 330n may comprise a plurality of a particular type of sensor, such as a plurality of pressure/temperature sensors as previously described, or sensor elements 330a through 330n may comprise two or more different types of sensor elements configured to sense different types of parameters. For example, one sensor element 330a may be configured to sense pressure and temperature, while an adjacent sensor element 330b may be configured to sense temperature, pH and/or other parameters such as flow rate, dimensions, distance or other position information, or other parameters. It is further noted that, while shown in a linear configuration on sheath 320, sensor elements 330a through 330n need not be positioned in this way (as shown in FIG. 3A), and may be disposed around the circumference or longitudinal axis of sheath 320, and/or may be positioned in other ways, such as adjacent to each other around the circumference of the sheath 320, on or near the optical port 224, or in other positioning arrangements such as grid arrays, depending on the desired sensing profile.

In addition to a plurality of sensor elements 230a through 230n, sheath 320 may also include one or more fiducials or targets 340a through 340n, as shown in FIG. 3A, that are configured to provide a mark or indication of the position of the endoscope, sheath, and/or sensor element(s) during an endoscopy procedure. For example, fiducials 340a through 340n may comprise a reflective material, such as metal foils or other reflective materials, that reflect/illuminate during an X-ray image, scan (such as a CAT scan), MRI, ultrasound, or during other imaging processes that may be used in conjunction with the endoscopy procedure. As such, targets 340a through 340n may then be used to match or fuse the data provided by sensors 330a through 330n with endoscopy images or visualizations, as well as with other images or visualizations captured during the endoscopy procedure. It is also noted that one or more targets 340a through 340n may be used in an endoscope sheath such as sheath 220 as shown in FIG. 2A, in conjunction with a single sensor element 230, to facilitate identification of the position of sensor element 230 during the endoscopy procedure.

In another embodiment, a touch sensor, such as a capacitive touch element (not shown) may be incorporated in the endoscope sheath to facilitate positional identification or registration during an endoscopy procedure. For example, multiple capacitive elements may be incorporated into the endoscope sheath at fixed distances, and their capacitance may be used to identify how deeply the endoscope has been positioned within the body cavity (such as an airway like the nasal passages or throat).

Figure 3B:
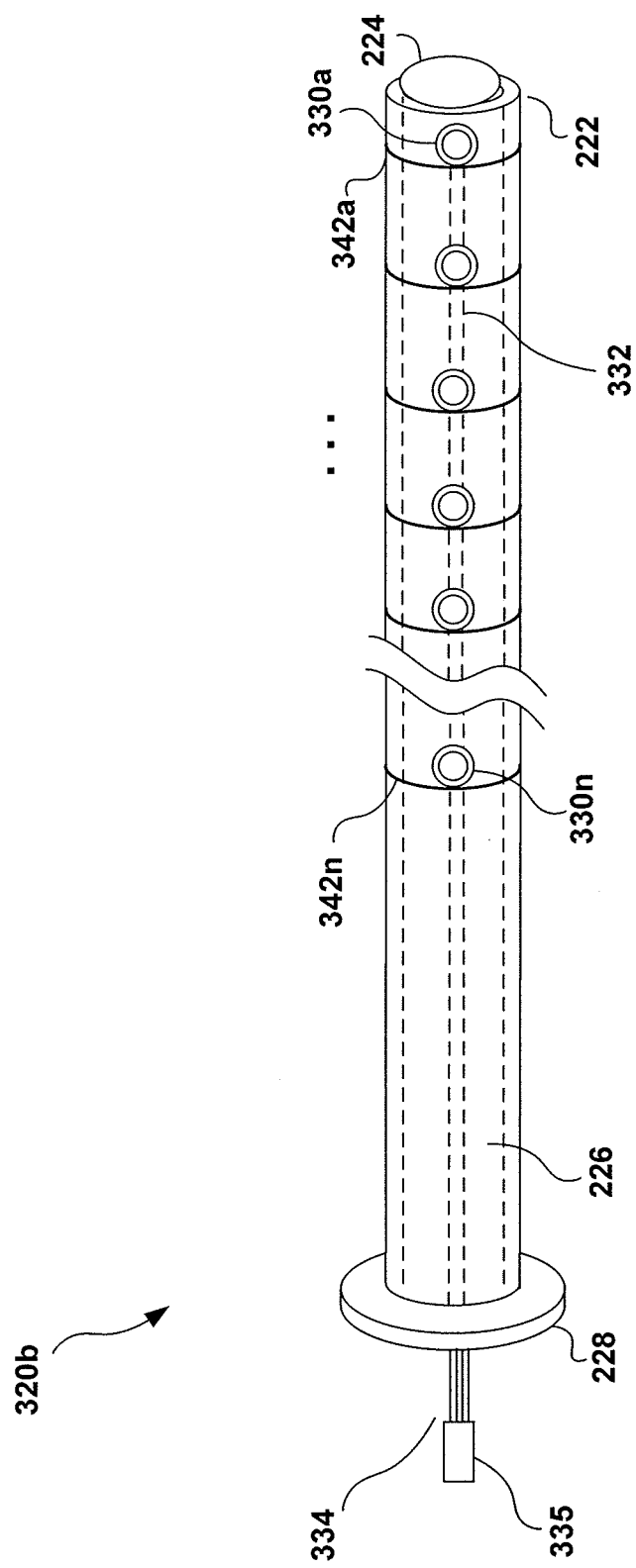
Figure 3C:
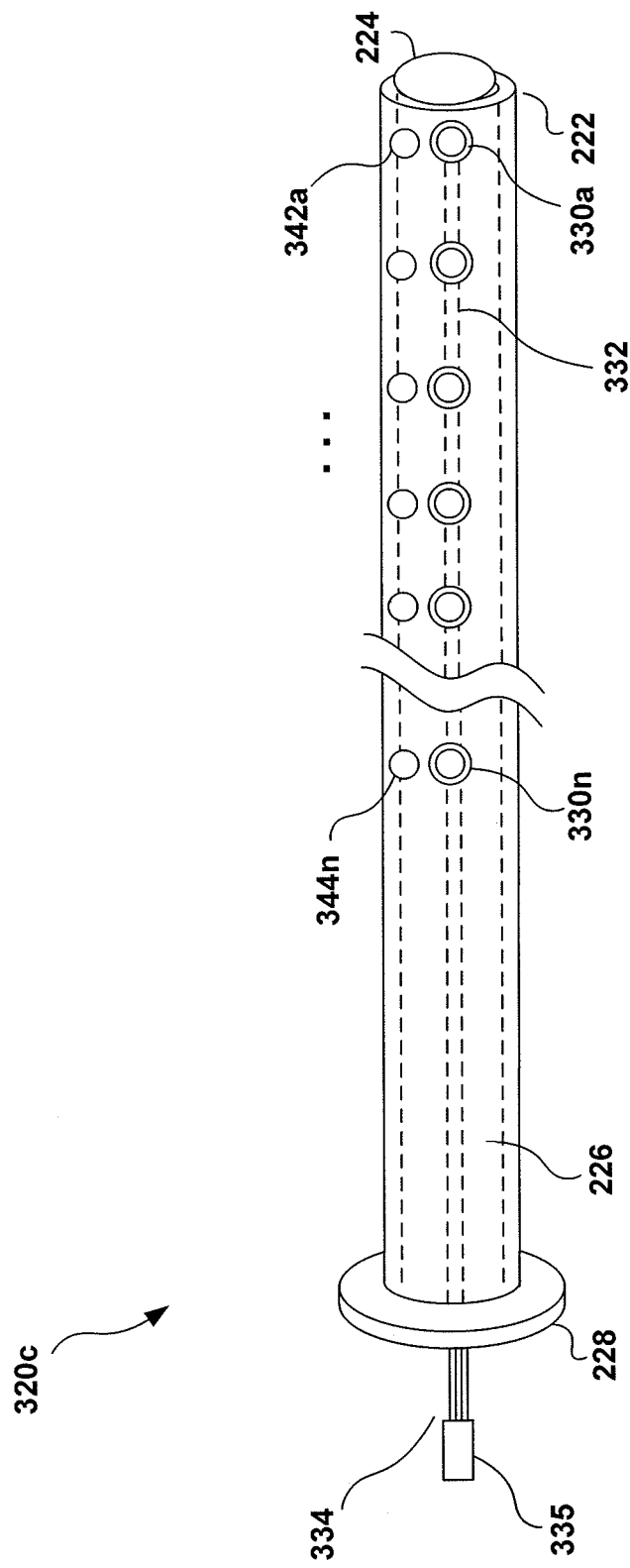

Attention is now directed to FIG. 3C, which illustrates details of another embodiment of the present invention. As shown in FIG. 3C, in addition to, or in place of, one or more of the features as shown in FIGS. 3A and 3B, a sheath 320c may include one or more position location elements 342a-342n. These elements are typically disposed on the endoscope sheath, or in some implementations the endoscope, to facilitate position location and registration of the endoscope and sensors, relative to the patient's airways. In a representative embodiment, element(s) 342 are a magnet configured to be used in conjunction with a Hall effect sensor such as the TLE4953 from Infineon Technologies or the A1174 from Allegro Microsystems, Inc, or another magnetic sensing element, so that the position of the sheath relative to the magnetic assembly can be detected by the magnetic sensing element. An example of this is further described below in conjunction with FIG. 3D.

Figure 3D:
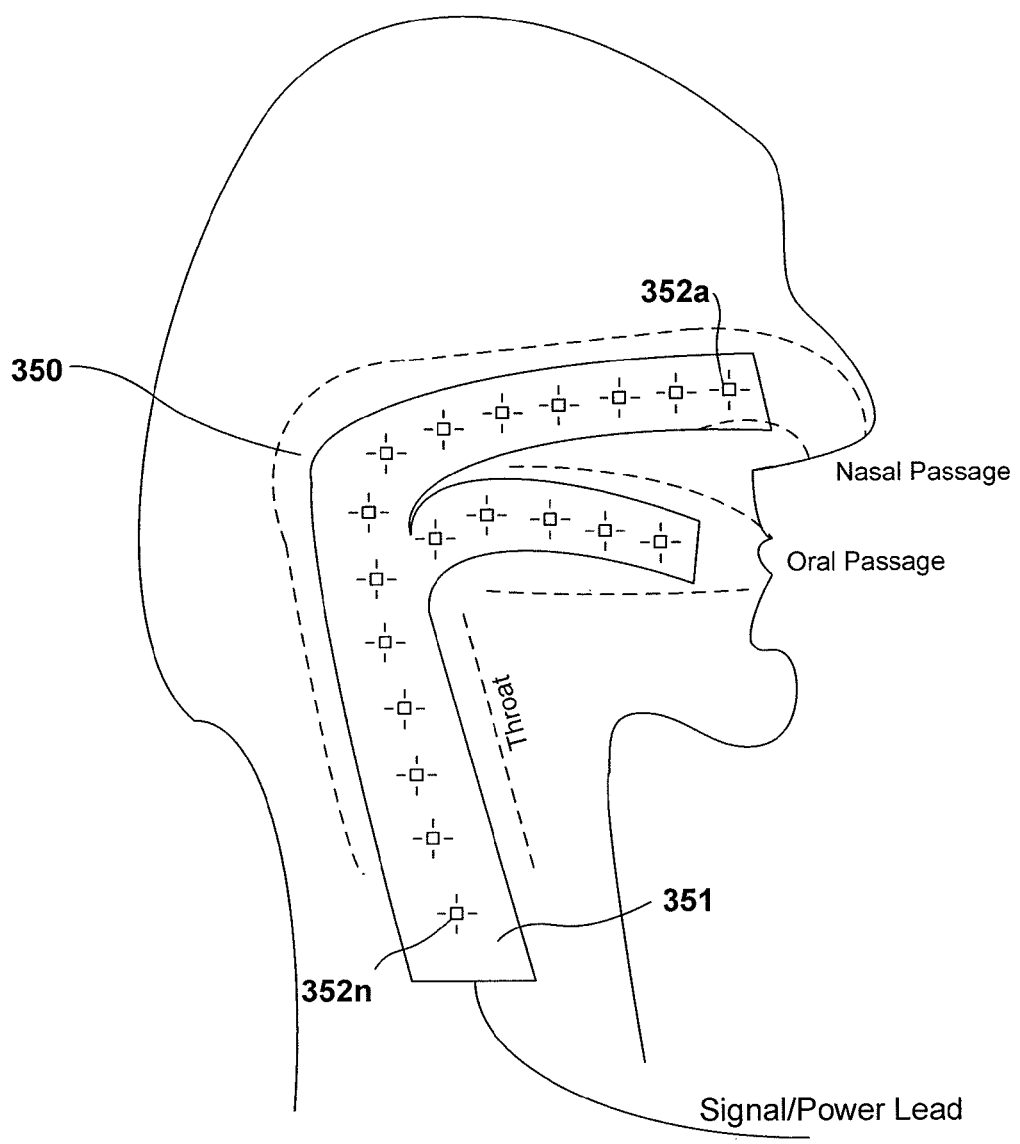
FIG. 3D illustrates one embodiment of a position sensing detector, in accordance with aspects of the present invention.

Attention is now directed to FIG. 3D which illustrates an embodiment of a position sensing assembly 350, which may include a magnetic sensing element such as Hall effect sensor in conjunction with a magnet, for use in determining the position of an endoscope during a procedure. As shown in FIG. 3D, position sensing assembly 350 (also denoted herein as a "position detector") may be used to determine the position of the endoscope apparatus within the patient during an endoscopy procedure. This may be done by sensing magnetic transitions as the Hall effect sensor moves past each magnet and is counted or otherwise registered by a processor, such as a microcontroller. Thereby, position sensing detector 350 is configured to locate, within the patient, the position of the endoscope, and the position or positions of sensor elements such as sensor 330a of FIGS. 3A-3C and/or the imaging element/camera of the endoscope. The output of position detector 350 may be provided to an endoscopy analysis module, such as system 530 as shown in FIG. 5. Position information obtained in conjunction with position detector 350 may then be used to fuse or map other sensory data, such as pressure, temperature, pH, airflow, etc., with an image or images of the airway of the patient and/or with other airway information, such as dimensions. This information may also be used to generate a cross-sectional or 3 dimensional view or image of the patient, along with the associated sensor information.

As shown in FIG. 3D, position sensing detector 350 may be used in conjunction with a magnet, fiducial, or other target mechanism disposed on the endoscope or on the endoscope sheath to map the endoscope position relative to the patient's body. In an embodiment based on a Hall effect sensor, which uses a Hall effect device and a magnet to sense the presence of the magnet relative to the Hall effect device, the position of the endoscope or particular endoscope sensors can be determined magnetically.

In one embodiment, position detector 350 includes a substrate 351, comprising a flexible plastic or other material, in which is incorporated a plurality of Hall effect sensors 352. The substrate 351 may be configured with an adhesive or other material allowing temporary attachment of the position detector 350 to the side of the patient's head, as shown in FIG. 3D.

The number of Hall effect sensors 352 included in a particular position detector 350 sensor array may vary, depending on the size of the patient, desired resolution, etc. For example, position detector 350 includes 19 sensors 352 as shown in FIG. 3D; however, other numbers of sensors may also be used. In addition, the array configuration of the sensors 252 may vary. For example, as shown in FIG. 3D, position detector 350 includes an array of sensors 252, with some sensors being positioned adjacent to the nasal passageway, some being positioned adjacent to the oral passageway, and some being positioned adjacent to the throat. However, in other embodiments, the arrangement and positioning of sensors may vary so as to provide sensing capability within a targeted portion of the desired airway or airways being examined. In one embodiment, a Hall effect sensor may be used and either deployed in on the sheath or the reference strip. Multiple magnets would be employed and spaced evenly along the strip. If a bipolar Hall effect sensor is used, each magnet may be alternately flipped from north to south. The mounting configuration of the magnets would be N S N S N S so that the direction as well as the distance of movement relative to the Hall effect sensor can be determined by the transition from north to south.

In operation, if a magnet is disposed on an endoscope sheath 320, such as magnet 342*a* of FIG. 3C (typically in the proximity of a sensor, such as sensor 330*a*, and/or the lens or imaging element of the endoscope and the endoscope is inserted in a patient, the position of the magnet 342*a* relative to the position detector 350 may be detected by determining which Hall effect sensor or sensors are activated by the magnet. This will occur when the magnet is in the vicinity of one or more of the Hall effect sensors 352, and the associated response can be mapped to a particular position on the position detector 350, and correspondingly to a location on a patient.

Position detector 350 should preferably be matches or registered to the patient so as to allow comparison of images and sensor data obtained from the patient during the endoscopy procedure. This may be accomplished by recording the location of the position detector 350 relative to the patient by a photograph or other imaging technique before, during or after the endoscopy procedure. Once the position detector 350 is registered to the patient, a map or other image of the position of the endoscope within the patient may be generated, with the map including position information, an image or images of the airway, cross sectional dimensions, sensor data and/or other test or measurement parameters. This may be done in system 530, as further described herein.

Figure 4A:
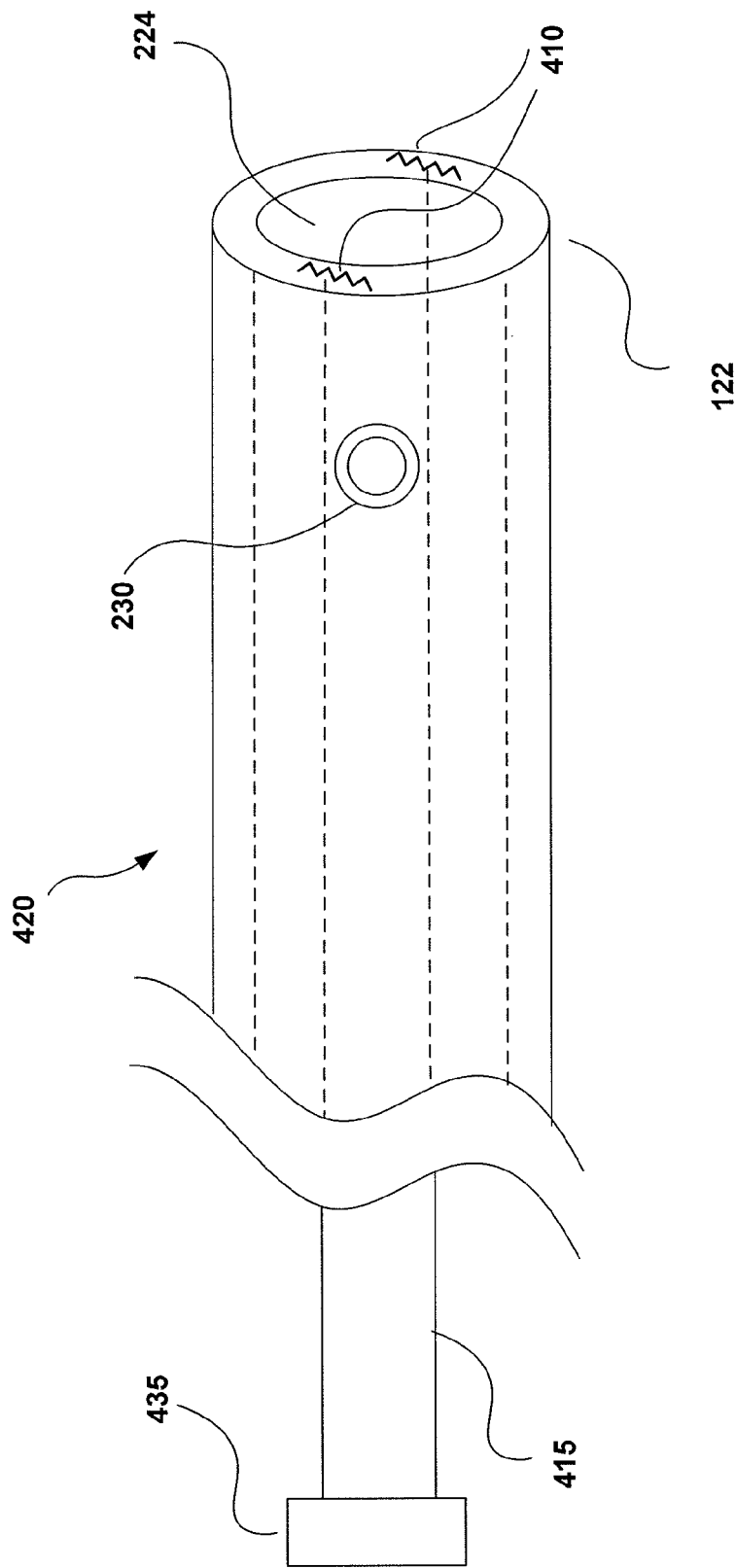
FIG. 4A illustrates one embodiment of an endoscope sheath heating element configuration in accordance with one aspect of the present invention.

Attention is now directed to FIG. 4A, which illustrates additional details of one embodiment of an endoscope sheath in accordance with aspects of the present invention. As shown in FIG. 4A, an endoscope sheath may include one or more heating elements 410 configured to heat an area of the endoscope or sheath to improve performance. These elements may be, for example, a thin layer of indium tin oxide (ITO) or other resistive material that may be electrically driven to heat the distal end of the sheath to reduce or eliminate moisture condensation or fogging. These heating elements may comprise resistive heating elements as are known or developed in the art. The heating elements may be disposed on the lens or lens area to improve visual clarity by alleviating condensation at the lens a cause of image blur. In one embodiment, the heating element may comprise an ITO (indium tin oxide) coating through which a current may be run.

In addition, one or more temperature sensors may be used in combination to implement closed loop control, where the internal temperature of the endoscope/sheath and/or lens or optical port area is regulated. This may be done as follows; first, a measurement is made of the internal temperature of the sheath, such as by using a temperature sensor mounted on the interior of the sheath and in contact with the endoscope or air pocket surrounding the endoscope. Then an external temperature measurement of the body cavity outside the sheath is made, and the internal and external temperatures compared. It is expected that the external temperature will typically be higher than the internal temperature, so a heating element disposed on or in the sheath is then energized to heat the sheath and endoscope to a temperature that matches or approximates the outside temperature (i.e., the body cavity temperature). The temperature sensors and heating elements may be coupled with a closed-loop control system, such as are known in the art, to automatically implement this process of temperature matching. In some embodiments the closed-loop control system may be directly incorporated in the sheath itself, in the form of a microcontroller or other microcircuit based implementation (such as on an FPGA, ASIC, etc.).

In other embodiments, some of the closed loop control elements may be implemented in the endoscope and/or on an external system electrically coupled to the element may be used in the cooling mode so as to implement internal cooling rather than heating.

Figure 4B:
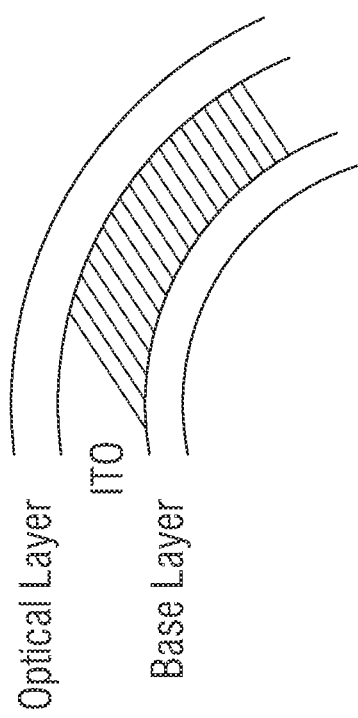
FIG. 4B illustrates one cross sectional view of an endoscope sheath heating element configuration in accordance with one aspect of the present invention.

FIG. 4B illustrates one configuration of a heating element at the distal end of an endoscope sheath. The heating elements 410 may be positioned in the endoscope sheath body 420 at or near the distal end 122, or at other locations in the sheath body. The heating elements 410 are typically used in an endoscopy procedure for providing heat to clear the optical port 224 (or other sheath surfaces or elements not shown) to facilitate improved imaging of the area under examination. It is also noted that, in some embodiments, cooling elements (not shown) configured to provide a cooling function similar to that of the heating elements 410 may also be used. Likewise, combination elements, such as Peltier junction elements, may also be used to provide both heating and cooling functions in some embodiments. Power wires 415, or other power distribution channels, may be used to provide power to heating element 410 from a connector element 435. Other associated elements, such as a temperature sensing element and associated power and wiring (not shown) may also be disposed in sheath 420 and used in conjunction with heating element 435 to monitor temperature or other conditions in the endoscope and/or body area under diagnosis.

Figure 5A:
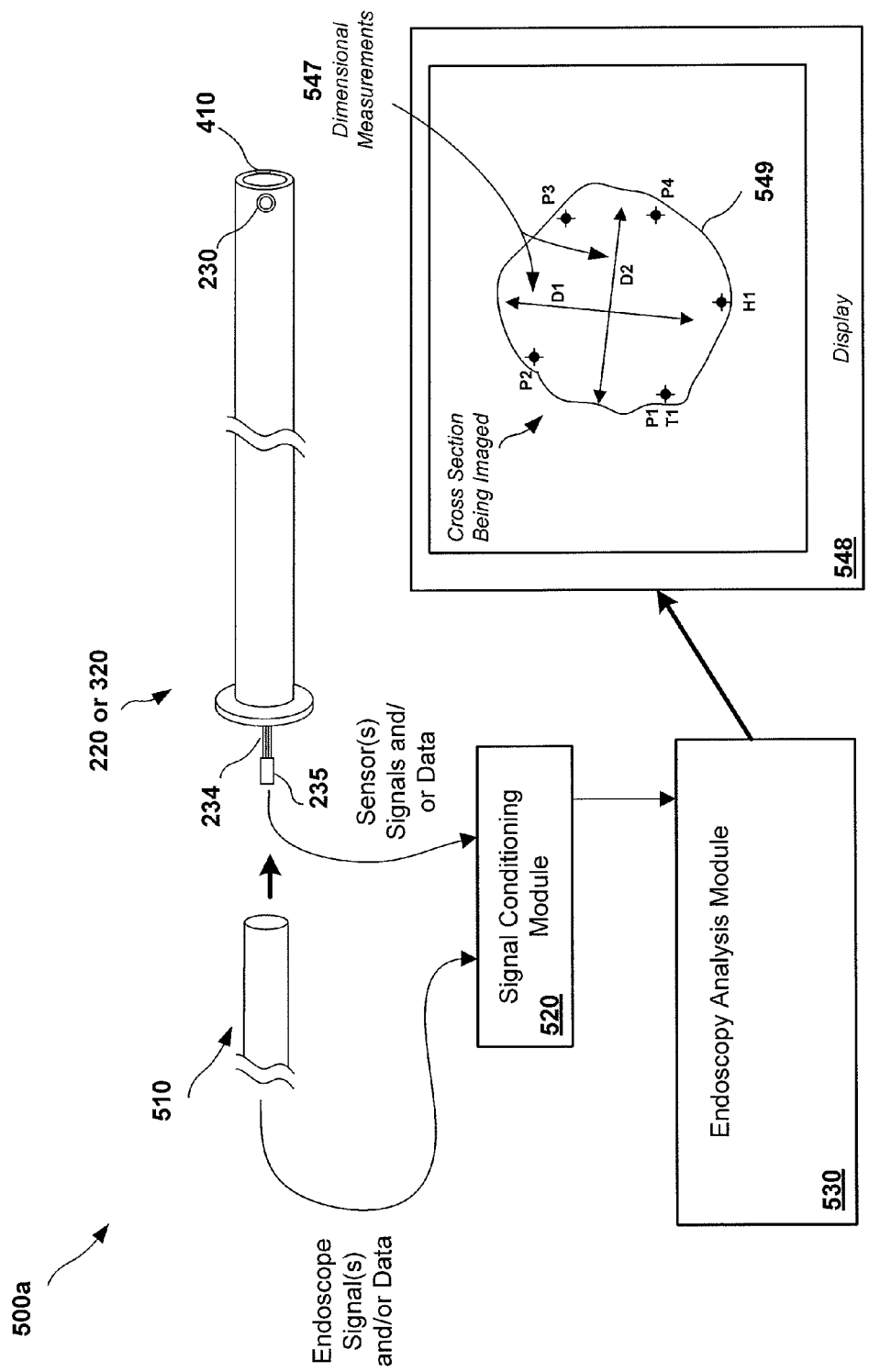
FIG. 5A illustrates one embodiment of a sensor enhanced endoscopy system in accordance with aspects of the present invention.

Attention is now directed to FIG. 5A which illustrates one embodiment of a system 500*a* for performing endoscopy using a sensor enhanced endoscope. System 500*a* may include an endoscope 510, with the endoscope being enclosed for the procedure using a sensor enhanced endoscope sheath 220 or 320 (such as are as shown in FIG. 2 and FIG. 3), along with an optional signal conditioning module 520 and a processing storage and display module ("endoscopy analysis module") 530. In typical embodiments the endoscope 510 and sheath 220 or 230 are separate components as described previously herein. However, as also noted previously, in some embodiments endoscope 510 may also include one or more sensors incorporated into the endoscopy body.

In order to process signals received from the endoscope 510 and/or the endoscope sheath 220 or 320, signal conditioning module 520 includes electronic circuitry for processing raw signals from the endoscope and/or the sheath and converting the signals to a standardized format for input into module 530 for further analysis, processing, display and/or storage of signals, images or other data. This conversion may include analog-to-digital conversion, signal format conversion or encoding, image processing, or other signal conditioning or processing. Alternately, module 530 may be configured for direct input of the raw output signals from the endoscope 510 and/or the sheath 220 or 230, with the signal conditioning module bypassed with respect to one or both of the endoscope and sheath outputs. System 500*a* includes a display element 548, which may be an LCD, plasma or other display technology as are known or developed in the art. Module 530 may receive the sensory data from sensor(s) 230 and may fuse this data with images received from the endoscope, with the fused sensor and image data then stored in module 530 or in another in another system (not shown). In addition, display 548 may be configured to provide a composite display presentation 549 as shown in FIG. 5A, where the image data, such as a cross section of an airway being imaged (as shown in FIG. 5A), is fused with the sensor data (in this example, pressure data P1-P4, temperature data T1, humidity data HT, as well as other sensory data (not shown) and displayed for use during a medical procedure or for future use. In addition, dimensional data 547, such as airway dimensions D1 and D2, may be collected from the endoscope or endoscope sheath, associated and fused with the other sensory information and stored together, and may be displayed on a display such as display 548 as shown in FIG. 5A.

Figure 5B:
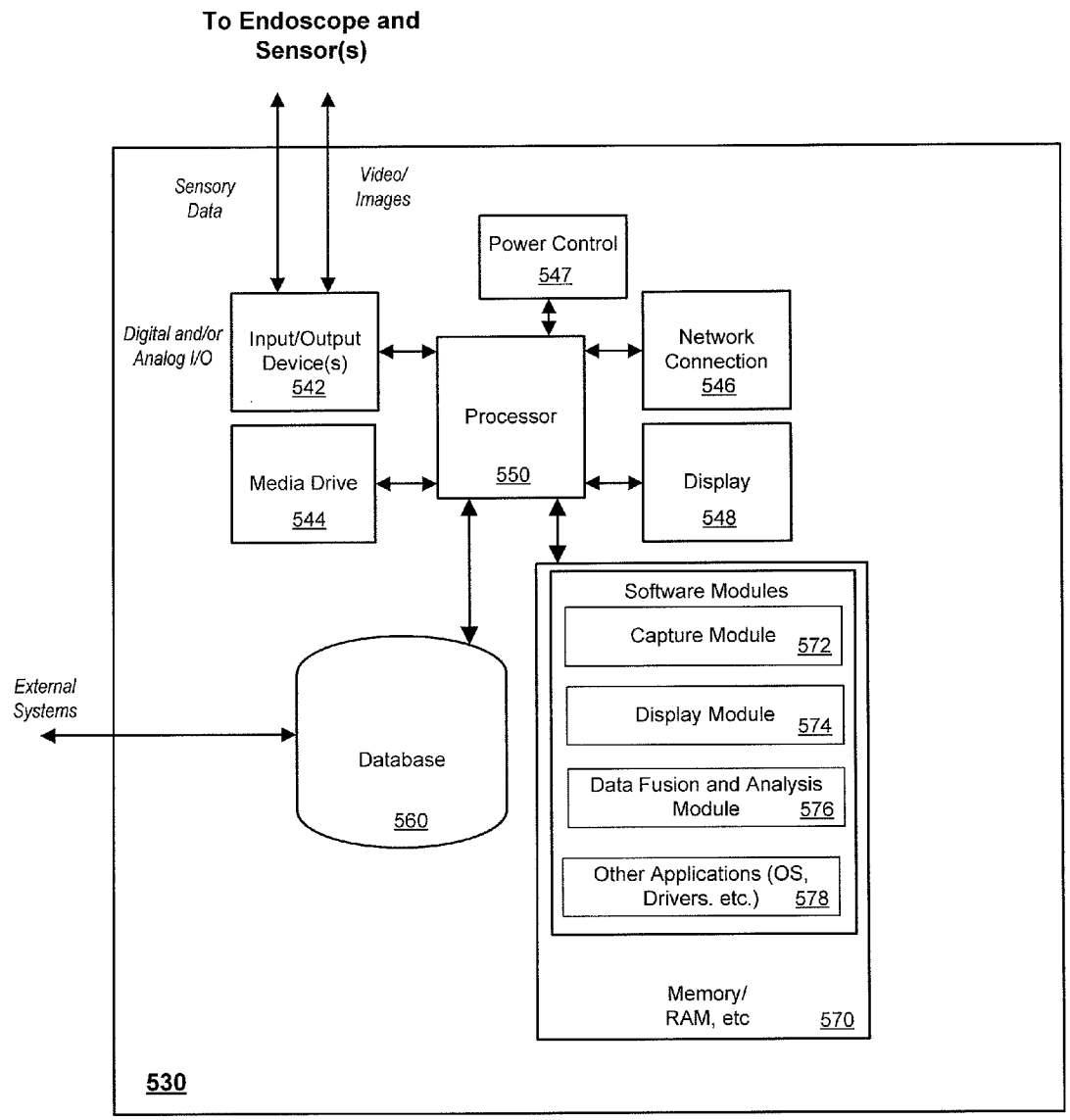
FIG. 5B illustrates one embodiment of a processing system for sensor enhanced endoscopy in accordance with aspects of the present invention.

FIG. 5B illustrates additional details of one embodiment of an endoscopy module 530 configured for receipt and processing of signals and data from a sensor enhanced endoscope system. Signals and data may include analog or digital sensory data, such as may be provided by the endoscope sheath and associated sensors and electronics, video or images as may be provided by the endoscope or other instrument, as well as other data and/or information such as may be provided by other sensors on a patient, or data or information from servers, databases or other systems, such as x-ray images, MRI images, or other data or information.

In a typical embodiment, module 510 includes one or more input/output (I/O) devices 542 configured to receive and transfer data or signals to and from the endoscope 510 and sheath 220 or 320 either directly or through signal conditioning module 520, which may include analog I/O functionality and/or digital I/O functionality. This may be done using circuits provided from companies such as Maxim, National Semiconductor as well as others. Module 530 may be configured to receive image or other visual data and fuse this data with the sensory data and or other data or information, such as clock or timing information.

Module 530 may also include one or more media drives 544 to receive input media data and information and provide media output (such as a read/write CD drive, DVD drive, Blu-Ray or other readable and writable media device). Module 530 may also include one or more processors 550 configured to interface to other devices in module 530 and process, in accordance with one or more sets of machine readable instructions stored on a machine readable medium, such as a memory, a hard disk, CD or DVD, RAM, ROM or other digital storage media.

Module 530 may also include one or more databases 560 configured to store and provide data and information, such as text or graphics, images, videos, or other endoscopy related data or information. This may include records or other information associated with one or more patients undergoing endoscopy with system 530 along with associated images and sensory data. Additional elements of module 530 may include one or more network connection modules configured to provide network connectivity to module 530, such as through Ethernet, Firewire, USB, wireless networking (such as via IEEE-802.11 (Wi-Fi), Wi-Max, Cellular) or other networking technologies.

Module 530 may also include one or more display interfaces 548, along with one or more displays (not shown) such as computer or video monitors for displaying the endoscopy results and/or associated sensor data.

Module 530 also includes one or more memory spaces 570 configured to store one or more application program modules for facilitating receipt, processing, analysis, fusion, storage and retrieval of endoscopy images, data and associated sensory and other information such as is described elsewhere herein. In a typical operation, the processor controls power on of the endoscope and sheath sensors. This may be done in conjunction with a power control module 547 as shown in FIG. 5B. After power on when the endoscope, sheath instrumentation and any other data or information is available, the processor may then control acquisition of video and images from the endoscope, along with sensory data from the sheath, and fuse this information with any addition data or information, such as timing information, other sensory inputs, dimensional information, stored data or images, and the like. This information may then be aggregated and stored in the database 560 and/or memory 570. In addition, the information may then be displayed on a display device, such as is shown in FIG. 5A. The collected and fused information may also be stored on media using media drive 544.

Figure 6A:
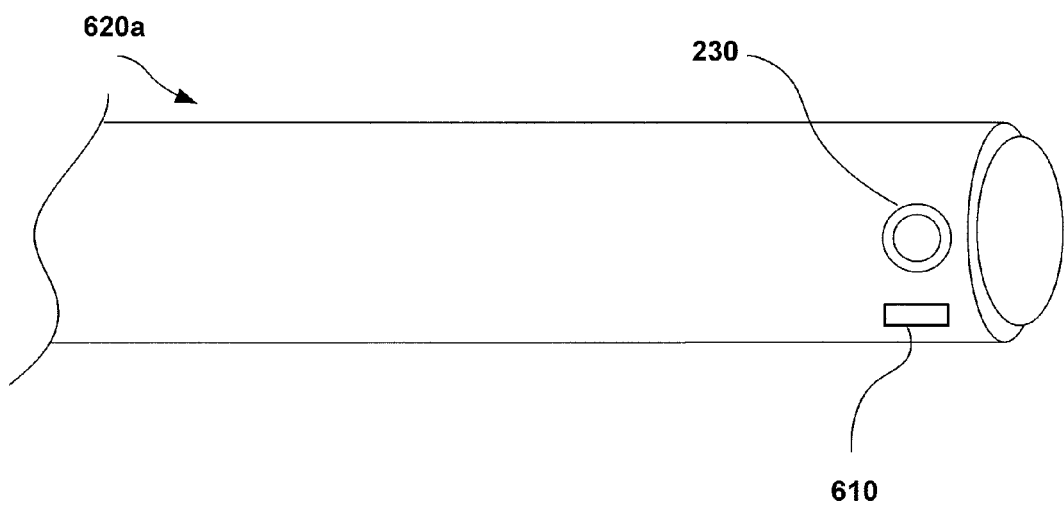
FIG. 6A illustrates an endoscopy system including a position location element in accordance with aspects of the present invention.

Attention is now directed to FIG. 6A, which illustrated details of an endoscope sheath 620a including a sensor 230 along with a position location element 610. As described previously with respect to FIG. 3D, the position location element can be a magnetic element, a Hall effect sensor, a metallic element, or other position sensing element as known or developed in the art. When used with the apparatus illustrated in FIG. 3D, the position location element may be used to identify a position of a sheathed endoscope relative to patient body features or other areas being examined by endoscopy.

Figure 6B:
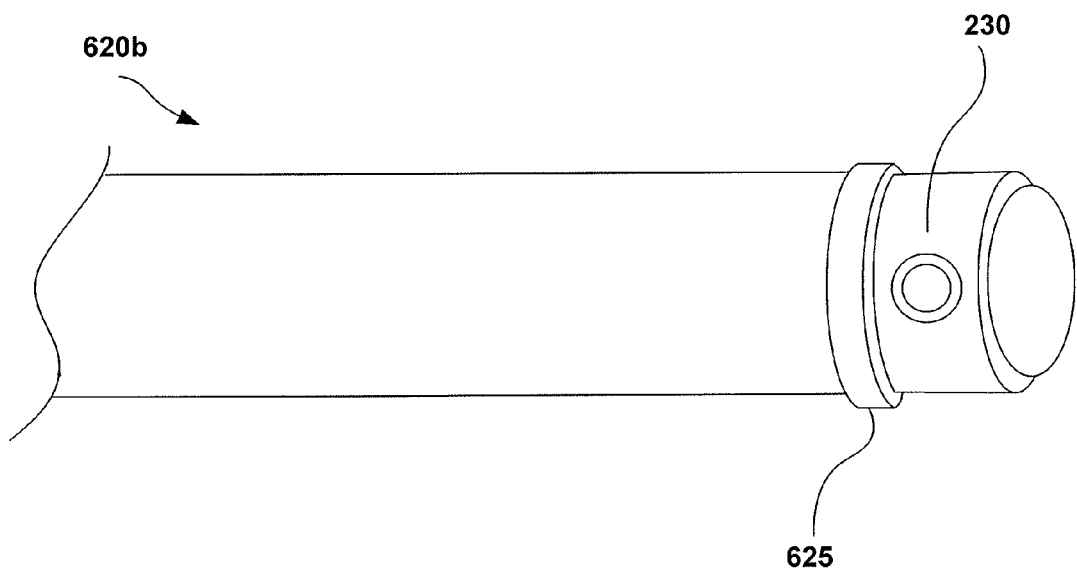
FIG. 6B illustrates one embodiment of an endoscope sheath with ultrasonic measurement apparatus, in accordance with aspects of the present invention.

Attention is now directed to FIG. 6B, which illustrates an embodiment of a sheath 620b including a measurement element, in this case an ultrasonic measurement element 625 Measurement element 625 may be disposed in the sheath body relatively close to the distal end or sensor element(s) 230 so as to make dimensional measurements associated with the endoscopy images and sensory data collected by the endoscope system. For example, dimensional values 547 may be collected and mapped to or fused with data provided on an image display such as is shown as D1 and D2 in display element 548 of FIG. 5A.

Figure 7:
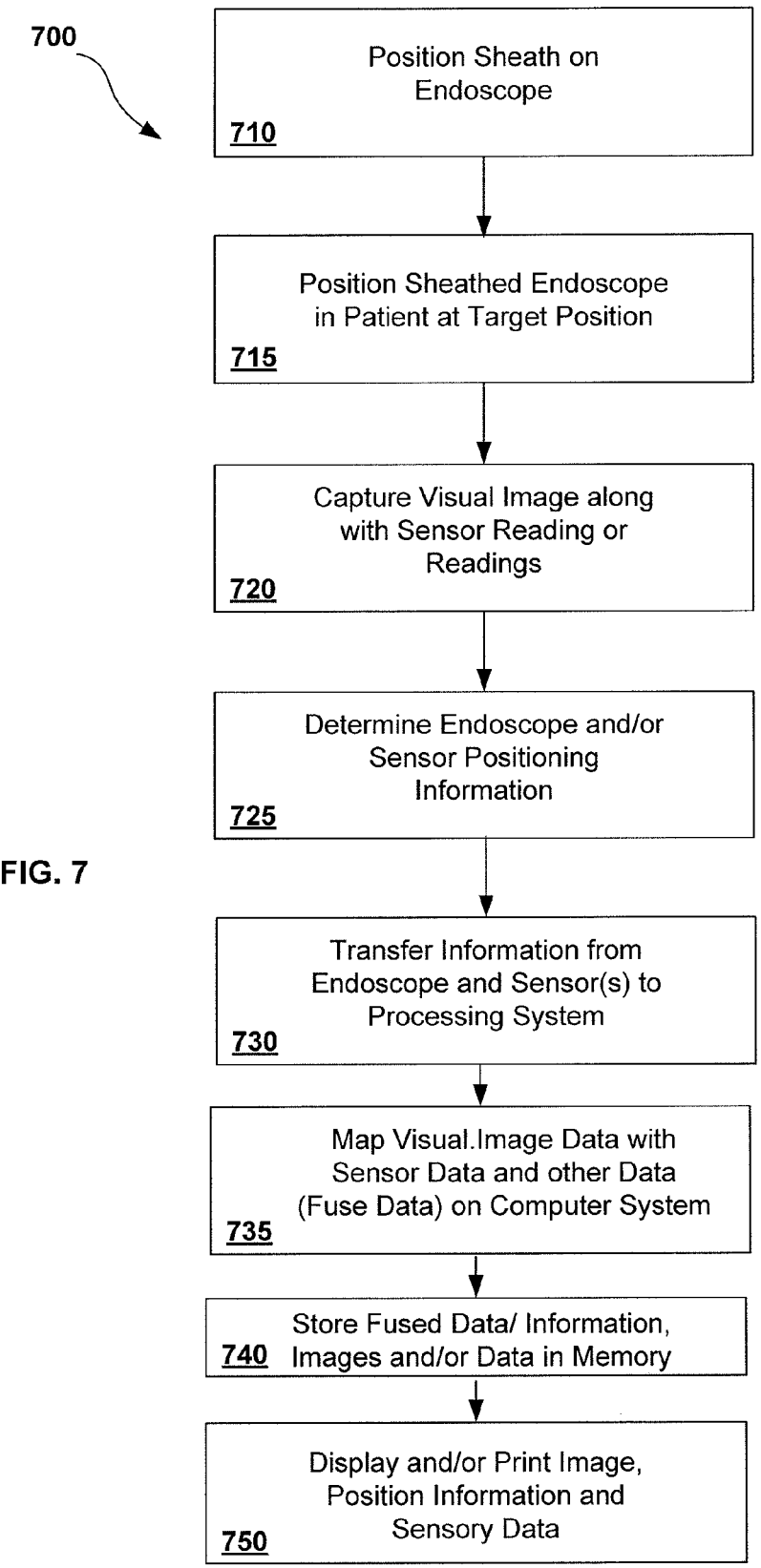
FIG. 7 illustrates one embodiment of a method of using a sensor enhanced endoscopy system in accordance with aspects of the present invention.

Attention is now directed to FIG. 7 which illustrates one embodiment of a process 700 for performing an endoscopy procedure, in accordance with aspects of the present invention. It is noted that process 700 includes particular stages; however, these stages are shown for purposes of illustration, not limitation. Other processes having more, fewer, or different stages are also within the spirit and scope of the present invention. In addition, it is noted that one or more stages of process 700 may be performed with an endoscopy system such as those illustrated in FIG. 2A through FIG. 6; however, other embodiments of the process 700 may be performed with additional and/or different elements than those shown in the figures.

Turning to FIG. 7, process 700 may begin at a start stage 710, where an endoscope sheath, typically a sheath including one or more sensor elements such as shown in FIG. 2 and FIG. 3, with the sensors including one or more pressure sensors, is positioned on the endoscope. In some embodiments an endoscope having embedded sensor, rather than sheathed sensors, may alternately be used. In either case, at stage 715, the endoscope is positioned in the patient's body at a desired location by a medical professional, such as a medical doctor. For example, it may be desirable to position the sheathed endoscope in an airway, such as the nasal passage or the back of the throat, to observe airway restrictions or other airway conditions. At the same time, other imaging devices, such as CT scams, X-ray imaging, MRIs, and/or other imaging technologies may optionally be used to further observe the airway and positioning of the sheathed endoscope during the procedure. It may be desirable to use the imaging capabilities of targets or fiducials (such as fiducials 340 shown in FIG. 3), or positional sensors (such as shown in FIG. 6A) to monitor the position of the endoscope and/or specific sensors such as sensors 320 or 330.

At stage 720, visual information is captured by the sheathed endoscope, along with one or more sensor measurements. The sensor measurements may include sensor data such as pressure readings at one or more points in the airway under observation. Likewise, other sensor readings, such as airflow, airway circumference, temperature, pH, or other parameters may also be measured simultaneously and/or sequentially with the endoscope imaging visualizations and optional external imaging. At stage 725, location and/or positional information of the endoscope may be determined and/or registered alone or in conjunction with the other imaging systems (such as by recording the positional information on a CT scan, MRI and the like). The information obtained by the sensor, as well as any associated endoscope information or data, may then be transferred at stage 730 to the processing system, such as system 530 shown in FIG. 5A and FIG. 5B. This may include transfer of the information obtained by the sensor (and/or endoscope) to a signal conditioning module to buffer and/or condition the data obtained by the sensor(s) and/or endoscope before transferring it to system 530. When the data and information from the endoscope and sensor have been transferred to the processing system 530 it may then be associated at stage 735, such as by storing the images obtained by the endoscope with the associated sensor readings (such as pressure, PH, temperature, dimensional measurement, etc.), further processed, and/or analyzed. The received sensor and/or endoscope data, along with any associated or processed data, may then be stored in a memory of the system 530 for further use.

Figure 8:
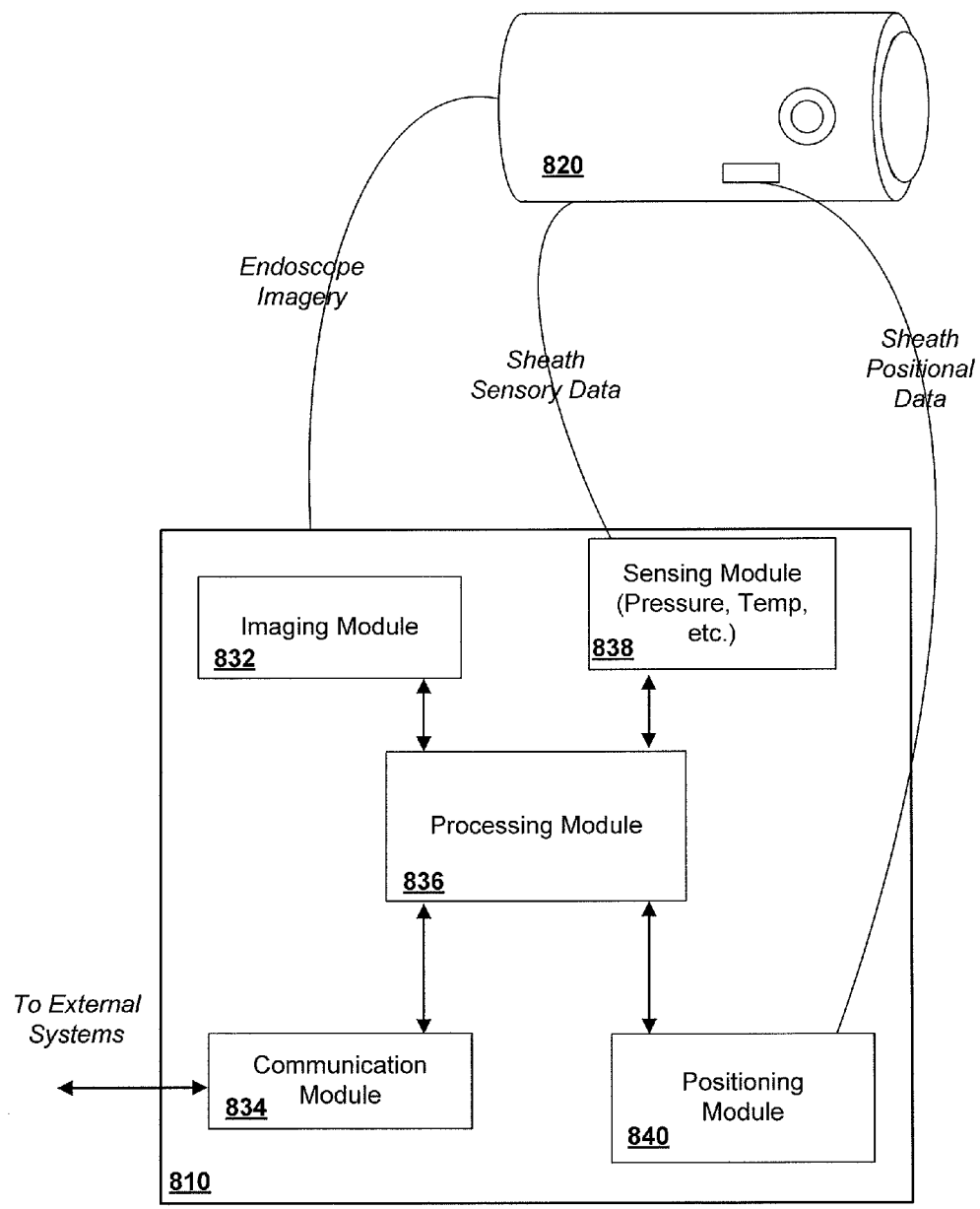
FIG. 8 illustrates details of an embodiment of an electronics module for use in processing data and information received from an endoscope and smart sheath.

FIG. 8 illustrates details of use of a smart sheath 820 disposed on an endoscope in conjunction with an endoscopy analysis module 810 configured to fuse endoscopy imaging data with sensory data. Module 810 may include multiple sub-modules, including an imaging module 832, configured to provide imaging data and/or display information from an endoscope imaging element, a communications module 834 configured to communicate data and/or other information from the smart sheath to other modules or systems. A sensing module 838 may be included to receive and process sensor information from one or more sensor elements disposed in the smart sheath, which may include temperate sensors, pressure sensors, PH or other chemical sensors, airflow sensors, conductivity sensors or other sensors as are known or developed in the art. A position module 840 may be included, with the positioning module configured to determine position based on information received from the smart sheath and/or aid in positioning the endoscope. The fused data may be stored in a memory and/or provided to other modules or systems via the communication module 834.

Figure 9A:
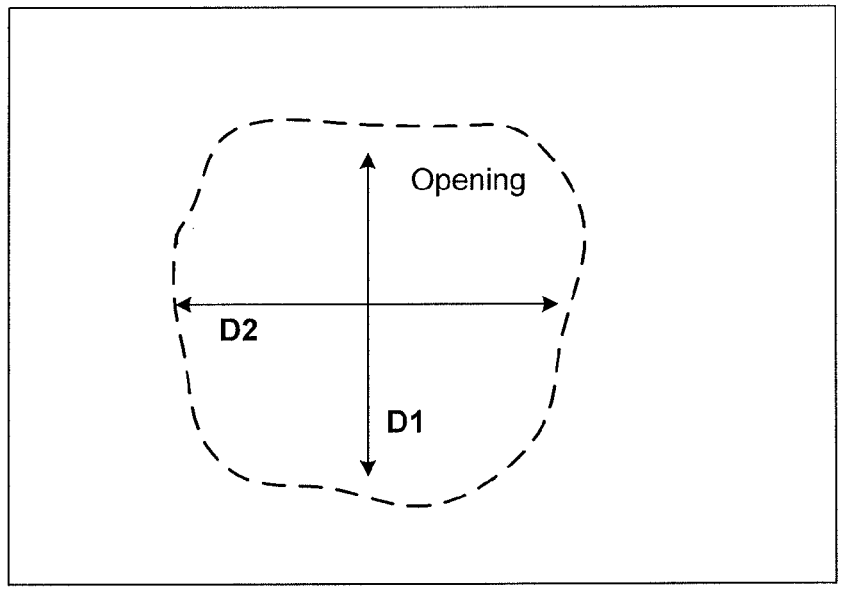
FIGS. 9A and 9B illustrate details of a cross-sectional sensor profile as may be generated by a smart sheath.
Figure 9B:
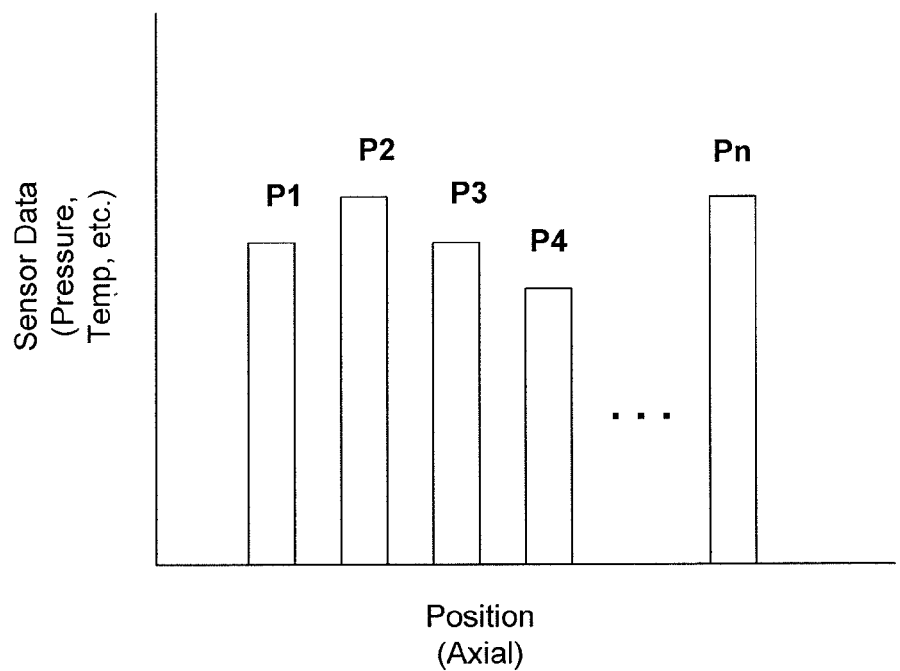

FIGS. 9A and 9B illustrates details of an embodiment of a smart sheath endoscopy system including a cross sectional sensor reading taken at positions axially disposed around the smart sheath. In particular, a smart sheath may be configured with a plurality of sensor elements as shown in FIGS. 3B and 3C, with a corresponding pressure profile then determined and mapped to the body cavity under examination. The mapping may be done in conjunction with imaging of the body cavity such as may be done using an image element of the endoscope. Dimensional information, such as D1 and D2, may be collected as described previously herein and associated with the pressure profile or other sensory information, with the results being stored in a memory and/or displayed such as shown in FIG. 5A. During medical or other endoscopy procedures, the endoscope may be moved and the movement registered and associated data collected, such as described previously with respect to FIG. 3D, or may be collected at a fixed endoscope position, which may include data collection from arrayed sensors such as shown in FIGS. 3A-3C.

In another aspect, in some embodiments a smart endoscope sheath may include, in addition to one or more sensors, a leak detection mechanism configured to detect leaks in the body of a sheath. This may be done as part of a sheath testing process and/or while use on an endoscope during a medical procedure. Detected leaks may be indicated on a display, such as display 548 as shown in FIG. 5A, and/or on an audible or visual alarm coupled to the endoscope or sheath (now shown). In addition, data associated with the leak may be collected and stored in the endoscope analysis module or in other systems.

Turning to the figures, FIG. 10 illustrates an example of a leak 1030 in a sheath body (not to scale). A leak such as shown in FIG. 10 may expose the endoscope and/or the patient under examination to contamination by pathogens, chemicals and the like. In non-medical procedures, a leak may expose an endoscope to similar contaminants, and/or to corrosives, toxins, etc. Consequently, it may be advantageous to incorporate leak detection capabilities into the smart sheath and the associated endoscopy system.

FIGS. 11A-11C illustrate details of one embodiment of a leak detection apparatus for use with a smart sheath using electronic leak detection sensing. A smart sheath 1120 may include one or more sensor elements 230, and may further include a conductive material 1135 disposed on or in proximity to the inner surface of the sheath body 1125, within the cavity for receiving the endoscope. Alternately, or in addition, in some embodiments additional conductive material may be disposed on an exterior surface of the sheath body (not shown).

As shown in FIGS. 11B and 11C, the conductive material 1135 may be disposed on all or most of the inner surface of the sheath to form an electrode. The conductive material may be a material deposited or coated on the inner surface of the sheath, and in some embodiments may be a conductive gel or similar material. Alternately, the conductive material may be a metallic coating or other conductive coating. In some embodiments, only a portion of the inner surface of the sheath may have the conductive material deposited thereon. This may be, for example, in a grid or other pattern on part of the inner surface. The conductive material may be used in conjunction with a leak detection circuit to detect leaks in the endoscope sheath body.

Figure 12A:
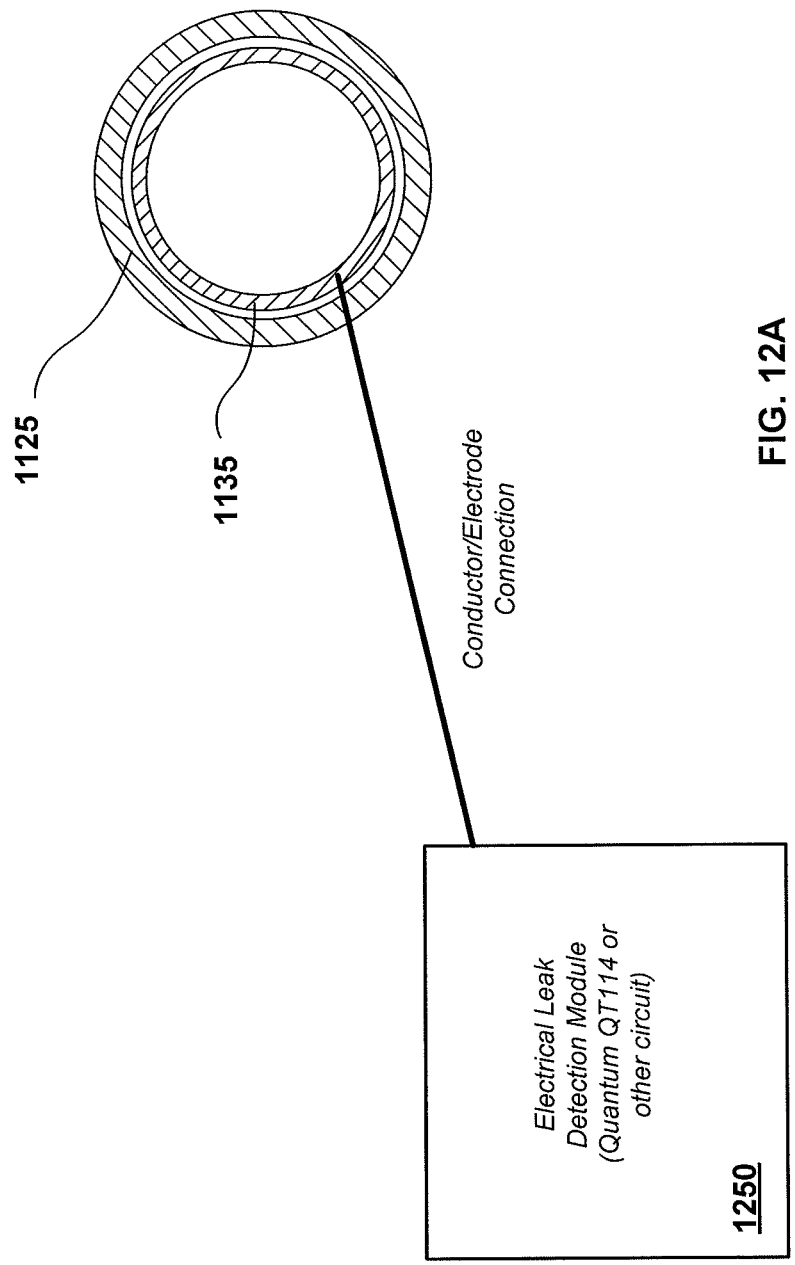
FIGS. 12A-12C illustrate details of embodiments of electrical leak detection details that may be used in conjunction with the sheath as shown in FIGS. 11A-11C.

FIG. 12A illustrates details of a leak detection apparatus including module 1250 configured to detect a leak in a smart sheath body, along with a conductive material 1135 as shown in FIG. 11. In one exemplary embodiment, module 1250, in conjunction with conductive material 1135, comprises a current flow or ion flow detection circuit, which may be implemented using elements described herein or as shown in the patents previously incorporated herein. In an exemplary embodiment, when a leak occurs, a conductive or partially conductive material, such as a saline bodily fluid, contact the conductive material, resulting in current flow. The leak detection circuit may be configured to detect this flow and thereby sense a leak. Alternately, in some embodiments, other circuits for electrical detection of leaks as are known or developed in the art may be used.

Figure 12B:
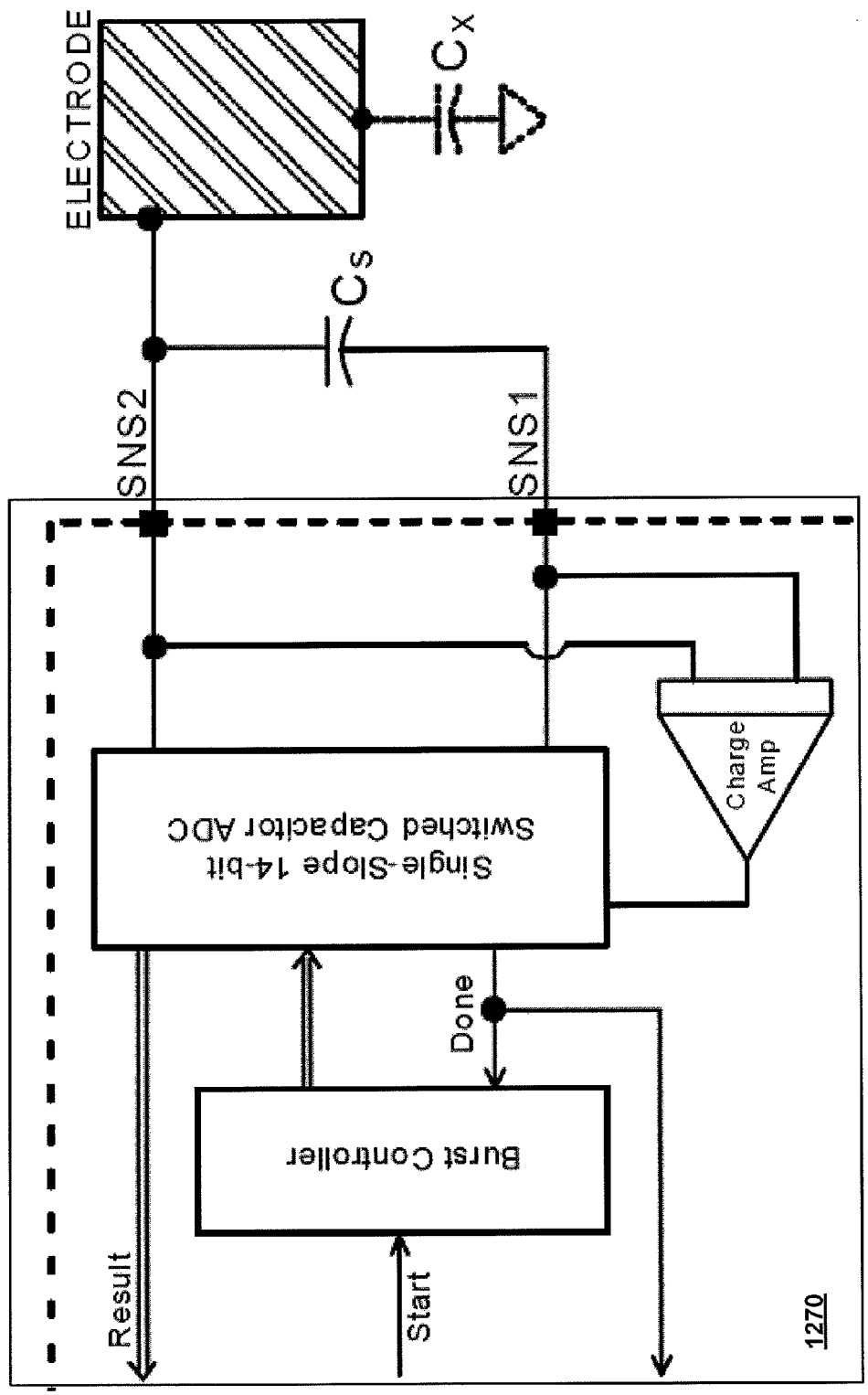

FIG. 12B illustrates one embodiment of a leak detection circuit 1270 that may be used in conjunction with the sheath 1120 for detection of leakage. Leak detection circuit 1270 may be part of a leak detection module such as module 1250 of FIG. 12A. In this implementation, the conductive material comprises an electrode that is coupled to the circuit 1250 to detect current flow associated with a leak. Other electrically based leak detection circuits may also be used in various embodiments. In some implementations, the sheath leak detection apparatus comprises only the conductive material/ electrode disposed on or in the sheath body. Alternately, in some embodiments the leak detection apparatus may comprise the electrode and a circuit such as circuit 1270, which may be on or connected to the sheath body.

Figure 12C:
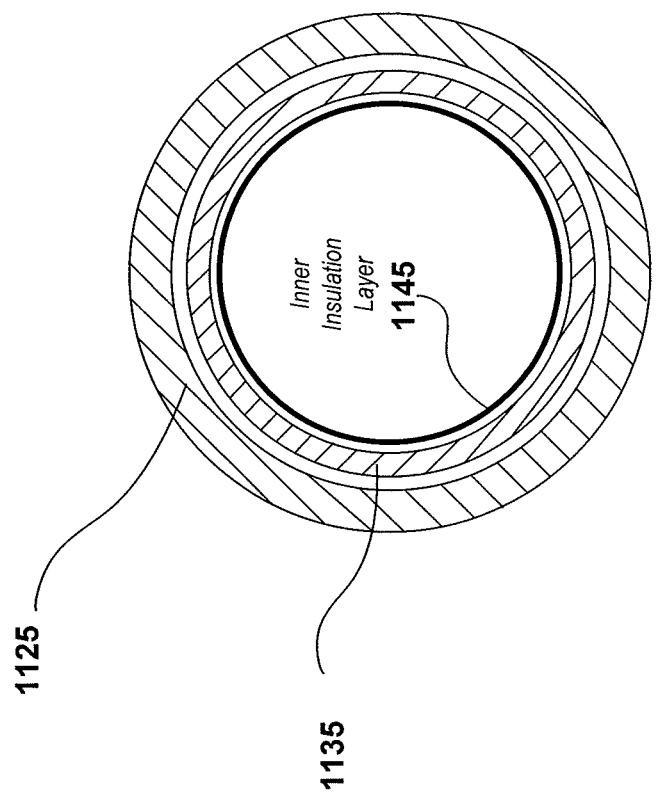

FIG. 12C illustrates details of another embodiment wherein an additional electrical insulation layer 1145 is disposed between the conductive layer 1135 and the cavity interior to the sheath. This configuration may be useful when the endoscope exterior is a metallic or other conductive material.

FIG. 13 illustrated details of an alternately embodiment of a leak detection apparatus using a pressure sensing element to provide pneumatic leak detection sensing. The pressure sensing element may be a pressure sensor 230 as shown in FIG. 13, which in some implementations may be common with or shared with the pressure sensing functions described previously herein. Alternately, the pressure sensing element may be a separate element. In some implementations, a flow sensor, rather than a pressure sensing element, may be used for pneumatic leak detection. In either case, the sensing element is configured to detect a signal associated with a leak in the sheath body where air or liquids are moving through the leak. To facilitate this, a sealing mechanism 1325 is typically included at the proximal end of the sheath 1320. The sealing mechanism may be an elastic element, an o-ring or other sealing element, a clamp, or other sealing mechanisms known or developed in the art.

In addition, a pressure supply control module 1350 may be included to provide a gas or liquid supply and associated gas or liquid pressure via a pressure supply line 1330 to the space between the inner surface of the sheath 1320 and the endoscope 110. Module 1350 may be configured to supply a source of gas pressure to the cavity between the inside of the endoscope sheath body and the exterior of the endoscope. Alternately and/or in addition, module 1350 may be configured with an airflow sensor to detect flow of a gas, such as may occur during a leak of the smart sheath. Leak detection may be determined by sensing a flow of gas or liquid out of the sheath and/or by monitoring pressure in the sheath cavity or by other pneumatic or hydraulic means.

Figure 14A:
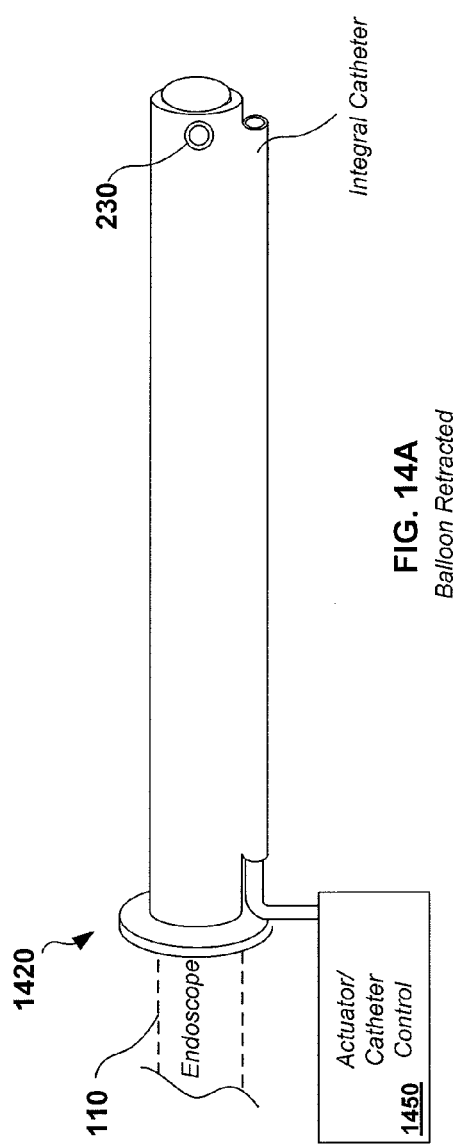
FIGS. 14A and 14B illustrate details of an embodiment of an endoscope sheath with integral actuator apparatus.
Figure 14B:
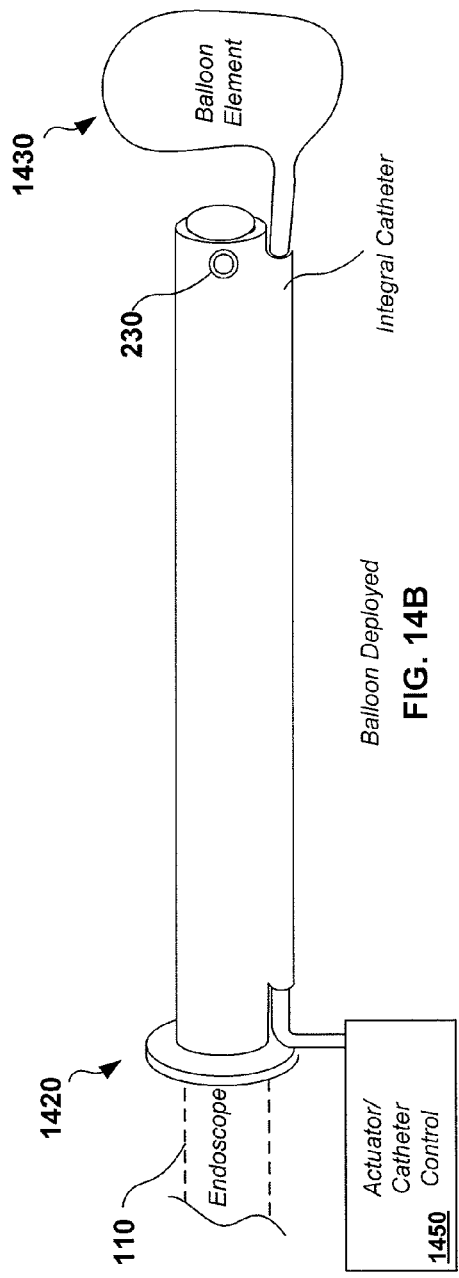

Attention is now directed to FIGS. 14A and 14B which illustrate one embodiment of an actuator apparatus incorporated in an endoscope sheath 1420. In sheath 1420, the actuator apparatus is a balloon catheter assembly, with the sheath body configured to allow for deployment or retraction of a balloon element 1430 for performing a balloon procedure such as thermal, RF, acoustic, ultrasonic, optical or other ablation treatments, or other balloon treatments such as expansion of a vessel or airway. The actuator may be controlled by an actuator control mechanism 1450, with the mechanism configured to deploy, retract and/or otherwise control the actuation element (e.g., the balloon element 1430). Control mechanism 1450 may include mechanical and/or electronic elements to facilitate control of the actuator.

Figure 15:
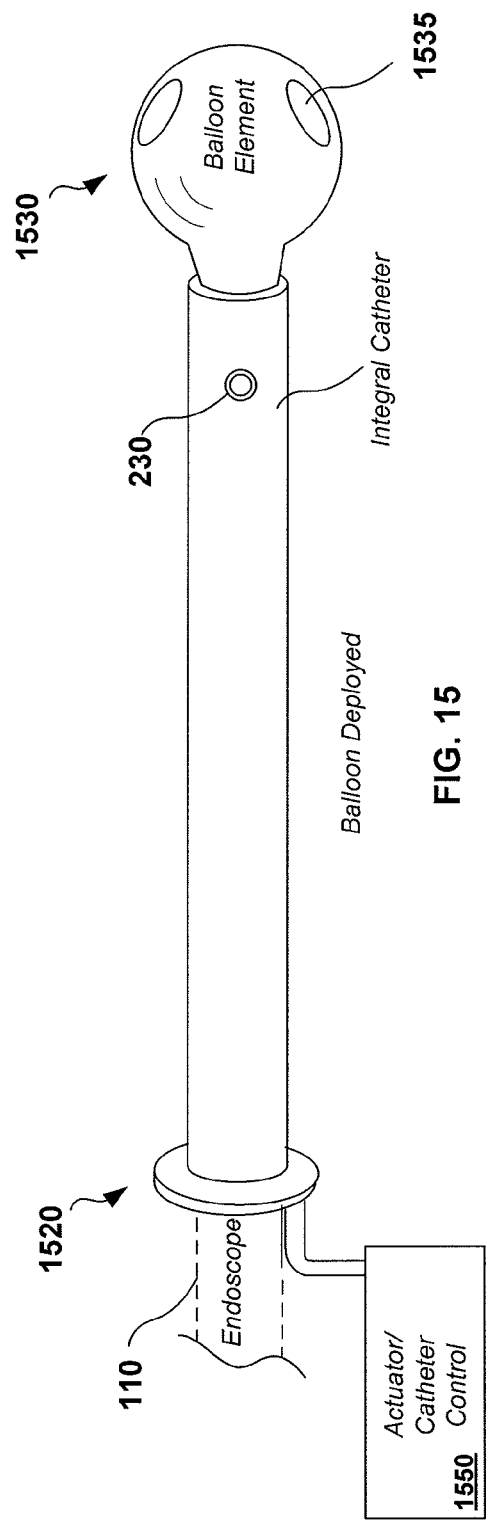
FIG. 15 illustrates details of an embodiment of an endoscope sheath with integral actuator apparatus.

FIG. 15 illustrates another embodiment of a sheath 1520 incorporating an alternate balloon catheter element 1530. In this embodiment, the actuator balloon 1530 may be clear or transparent, in whole or part, so as to provide additional imaging capability through any endoscope imaging elements at the distal end (not shown). Balloon 1530 may include lenses 1535 or other optical elements to further aid visualization of images collected by the endoscope. The actuator element on sheath 1520 may be controlled by an actuator control element 1550.

FIGS. 16A and 16B illustrate another embodiment of a sheath 1620 incorporating an alternate balloon configuration. In this implementation, the sheath body is configured so that balloon element 1630 may be deployment from an area in the side of sheath 1620 near the distal end.

FIGS. 17A and 17B illustrate another embodiment of a sheath 1720 incorporating an actuator in the form of a surgical instrument 1730. Instrument 1730 may include one or more scalpel elements 1740 or other surgical instrument as is known in the art. In this implementation, instrument 1730 is disposed in the sheath 1720 body and may be deployed or refracted as shown in FIGS. 17A and 17B. The actuator may be controlled by a control module 1750, which may facilitate electrical, mechanical, pneumatic, or other control of the surgical instrument.

In some embodiments, multiple actuator apparatus may be included in the sheath. For example, in one implementation, a first actuator apparatus may be a balloon catheter and a second actuator apparatus may be a stent placement apparatus. Stent placement apparatus are known in the art and are described in, for example, U.S. Patent Publications 20070250157, 20060276873, 20060200222, which are incorporated by reference herein, as well as in various other patents and publications.

As used herein, the word "exemplary" means "serving as an example, instance, or illustration." Any embodiment described herein as "exemplary" is not necessarily to be construed as preferred or advantageous over other embodiments, and is not intended to be limiting in any way unless otherwise noted.

Some aspects of the present invention may be embodied in the form or computer software and/or computer hardware/ software combinations configured to implement one or more processes or functions of the present invention as described and illustrated herein. These embodiments may be in the form of modules implementing functionality in software, firmware, and/or hardware/software/firmware combinations. Embodiments may also take the form of a computer storage product with a computer-readable medium having computer code thereon for performing various computer-implemented operations, such as operations related to functionality as describe herein, on one or more computer processors. The media and computer code may be those specially designed and constructed for the purposes of the present invention, or they may be of the kind well known and available to those having skill in the computer software arts, or they may be a combination of both.

Examples of computer-readable media within the spirit and scope of the present invention include, but are not limited to: magnetic media such as hard disks, floppy disks, and magnetic tape; optical media such as CD-ROMs, DVDs and holographic devices; magneto-optical media; and hardware devices that are specially configured to store and execute program code and/or data, such as application-specific integrated circuits ("ASICs"), programmable logic devices ("PLDs") ROM and RAM devices, Flash devices, and the like. Examples of computer code may include machine code, such as produced by a compiler, and files containing higherlevel code that are executed by a computer using an interpreter. Computer code may be comprised of one or more modules executing a particular process or processes to provide useful results, and the modules may communicate with one another via means known in the art. For example, some embodiments of the invention may be implemented using Java, C#, C++, or other programming languages and software development tools as are known in the art. Other embodiments of the invention may be implemented in hardwired circuitry in place of, or in combination with, machine-executable software instructions.

The claims are not intended to be limited only to the aspects shown in the drawings and described previously herein, but are to be accorded the full scope consistent with the language of the claims, wherein reference to an element in the singular is not intended to mean "one and only one" unless specifically so stated, but rather "one or more." Unless specifically stated otherwise, the term "some" refers to one or more. A phrase referring to "at least one of" a list of items refers to any combination of those items, including single members. As an example, "at least one of: a, b, or c" is intended to cover: a; b; c; a and b; a and c; b and c; and a, b and c.

The foregoing description, for purposes of explanation, uses specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description, not limitation. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

The invention claimed is:

1. A system for evaluating an airway, the system comprising:
   an endoscopy sheath having plural pressure sensors configured about and positioned on the external surface of the endoscopy sheath so that the plural pressure sensors are capable of providing pressure data related to the airway from more than one cross-sectional position about the endoscopy sheath;
   an endoscope for disposition within the endoscopy sheath, the endoscope for providing image data of the airway;
   a visual display; and
   an endoscopy analysis module configured to receive the pressure data related to the airway and the imaging data of the airway, the endoscopy analysis module comprising a processor, a data fusion module and a display module, the endoscopy analysis module being configured to provide information to the visual display in which the image data and the pressure data related to the airway are associated so that the visual display depicts, in one image, image data of the airway and pressure data related to the airway at more than one cross-sectional position about the image data of the airway.

2. The system of claim 1 further comprising a temperature sensor positioned on the external surface of the endoscopy sheath.

3. The system of claim 1 further comprising a pH sensor positioned on the external surface of the endoscopy sheath.

4. The system of claim 1 in which the endoscopy analysis module further comprises a position sensing module.

5. The system of claim 1 in which the endoscopy analysis module is configured to receive the pressure data and the image data via wires.

6. The system of claim 1 in which the endoscopy analysis module is configured to receive the pressure data and the image data by radio frequency.

* * * * *